US009148940B2

(12) United States Patent
Hawver et al.

(10) Patent No.: US 9,148,940 B2
(45) Date of Patent: Sep. 29, 2015

(54) INTERPOSER MECHANISM FOR A RETROFIT DIGITAL X-RAY DETECTOR AND METHODS OF USING THE SAME

(71) Applicant: Carestream Health, Inc., Rochester, NY (US)

(72) Inventors: Jeffery R. Hawver, Marion, NY (US); Peter A. Newman, Pittsford, NY (US)

(73) Assignee: Carestream Health, Inc., Rochester, NY (US)

( * ) Notice: Subject to any disclaimer, the term of this patent is extended or adjusted under 35 U.S.C. 154(b) by 403 days.

(21) Appl. No.: 13/713,054

(22) Filed: Dec. 13, 2012

(65) Prior Publication Data

US 2014/0169529 A1    Jun. 19, 2014

(51) Int. Cl.
*H05G 1/56* (2006.01)
*G01N 23/04* (2006.01)

(52) U.S. Cl.
CPC . *H05G 1/56* (2013.01); *G01N 23/04* (2013.01)

(58) Field of Classification Search
None
See application file for complete search history.

(56) References Cited

U.S. PATENT DOCUMENTS

| 6,078,639 | A  | * | 6/2000  | Heuscher    | 378/15  |
| 7,844,031 | B2 | * | 11/2010 | Newman et al. | 378/114 |
| 2006/0008054 | A1 | * | 1/2006 | Ohara       | 378/114 |
| 2007/0145280 | A1 | * | 6/2007 | Campbell    | 250/368 |

FOREIGN PATENT DOCUMENTS

| WO | WO 01/33921 | 5/2001 |
| WO | WO 2007/098920 | 9/2007 |
| WO | WO 2007098920 A2 * | 9/2007 |
| WO | WO 2007098920 A3 * | 2/2008 |

OTHER PUBLICATIONS

Anonymous, CDRPan for Panoramic Systems, Instructions for Panarami Corporation PC-1000, Oct. 2000, 22 pages, XP-002516607, Retrieved from the Internet: URL: http://www.shicktech.com/uploads/downloads/B1051101 Rev-.pdf
International Search Report, International application No. PCT/US2008/012872, Feb. 24, 2009, 3 pages.

* cited by examiner

Primary Examiner — Andrew Smyth

(57) ABSTRACT

Methods and apparatus are disclosed for obtaining an x-ray image from an x-ray imaging apparatus using a digital radiography receiver installed as a retrofit connection apparatus to adapt the x-ray imaging apparatus for use with the digital radiography receiver by using a receiver interface channel to communicating signals to and from the digital radiography receiver, using an operator actuated switch cover for at least an expose operator action of a manual operator control that is configured to generate at least an input expose signal, where the operator actuated switch cover is configured to resist the generation of the expose signal by the expose operator action of the manual operator control until a reset of the DR receiver is initiated and acknowledged.

19 Claims, 22 Drawing Sheets

- DETAIL A -

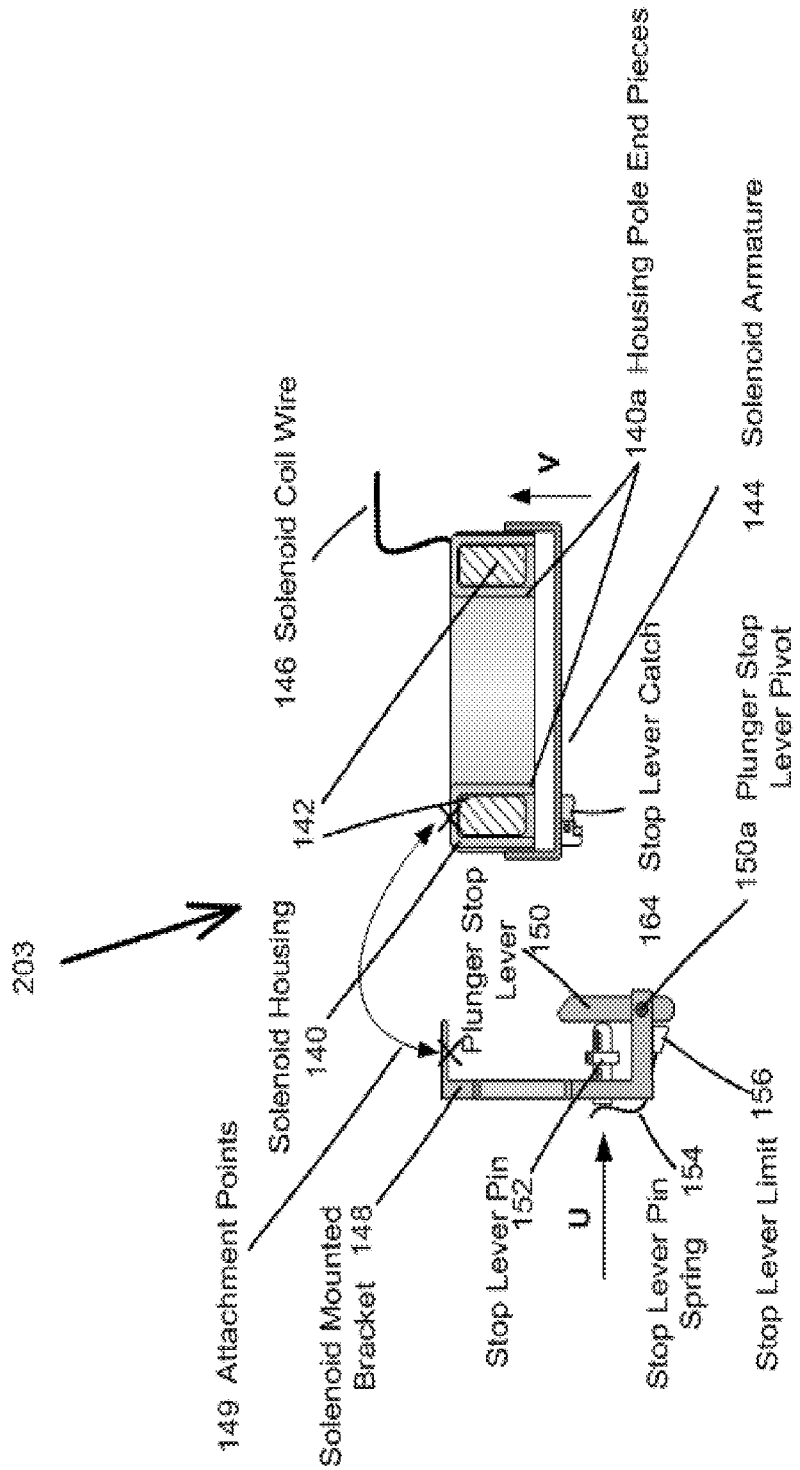

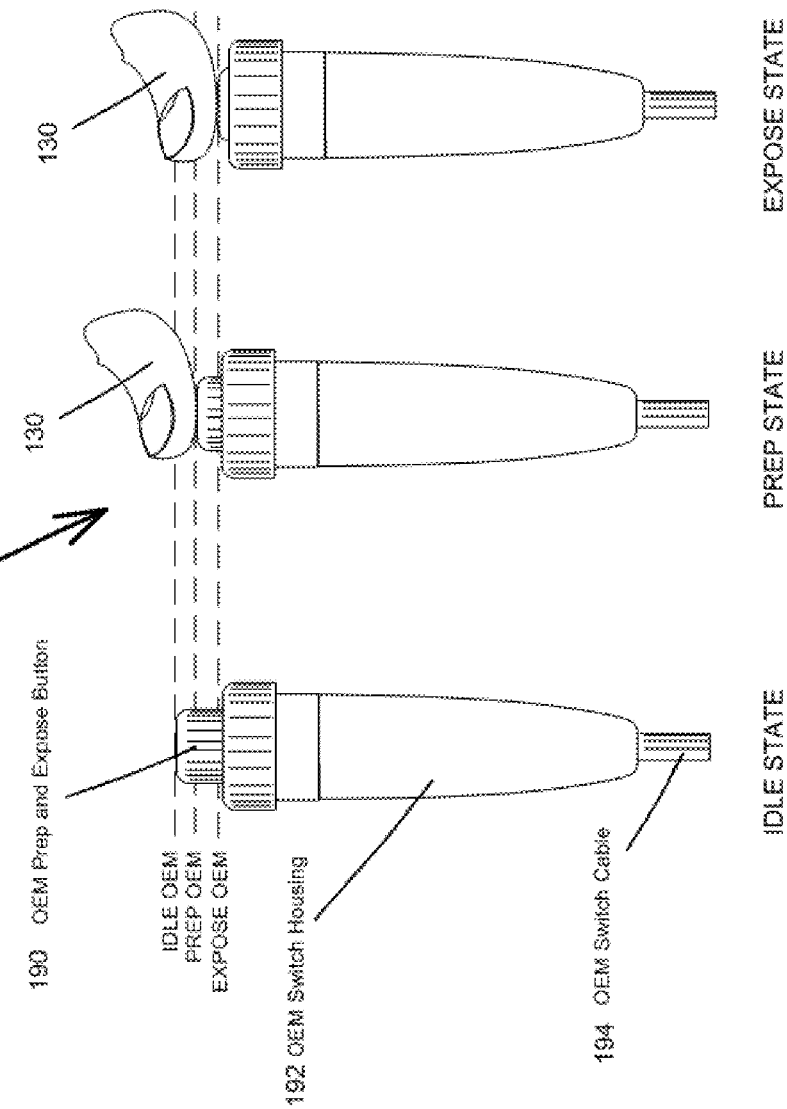

- DETAIL B -

INTERPOSER MECHANISM FOR A RETROFIT DIGITAL X-RAY DETECTOR AND METHODS OF USING THE SAME

FIELD OF THE INVENTION

The invention relates generally to the field of radiation conversion apparatus, and in particular to medical radiographic imaging and digital radiographic (DR) detectors, and more particularly to apparatus and/or methods for adapting the timing sequence of a conventional film-based and/or computed radiography (CR) x-ray imaging system for using a retrofit digital radiography (DR) detector.

This invention further relates to apparatus and/or methods for noninvasively interposing between components of existing x-ray system hardware and retrofit DR detector hardware without introducing new failure modes in the acquisition process where unintended x-ray exposure can occur.

BACKGROUND

While DR imaging systems have advantages over earlier film and CR systems, replacing such a earlier x-ray system can be very costly, thereby limiting the availability of DR systems as hospitals attempt to maximize their investment in older equipment and to extend its usable lifetime.

To meet the need for the improved capabilities offered by DR imaging, a number of companies that provide x-ray equipment offer retrofit configurations that allow a DR receiver panel to be used with existing x-ray components, in place of a film or CR cassette. Existing retrofit solutions, however, have one or more limitations.

Thus, there remains a need for a DR retrofit that has little or no impact on existing hardware, is less or minimally invasive with respect to the components of an existing x-ray system, and/or does not constrain an ability to use earlier film and CR imaging media in existing radiographic imaging arrays and/or methods for using the same.

SUMMARY OF THE INVENTION

An aspect of this application is to advance the art of medical digital radiography.

Another aspect of this application to address, in whole or in part, at least the foregoing and other deficiencies in the related art.

It is another aspect of this application to provide, in whole or in part, at least the advantages described herein.

An aspect of this application is to provide methods and/or apparatus to address and/or reduce disadvantages caused by the use of portable (e.g., wireless) digital radiography (DR) detectors and/or radiography imaging apparatus using the same.

An aspect of this application is to provide radiographic imaging apparatus and/or methods for making the same that can retrofit an existing film-based or CR x-ray imaging apparatus to capture an x-ray image using a DR receiver. A retrofit connection can be provided that adapts the x-ray imaging apparatus for use with a DR receiver. Certain exemplary embodiments can provide communicating signals to and from the DR receiver, rout at least an input expose signal from an operator control to the retrofit connection apparatus, and transmit at least an output expose signal to an x-ray generator. One exemplary embodiment can respond to the input expose signal by initiating a reset of the digital radiography receiver before transmitting the output expose signal to the x-ray generator (e.g., over a generator interface channel).

An aspect of this application is to provide radiographic imaging apparatus and/or methods that can provide a retrofit solution that is substantially non-invasive, reducing or eliminating the likelihood that inspection or re-certification of equipment by regulatory authorities would be required.

An aspect of this application is to provide radiographic imaging apparatus and/or methods that can provide a retrofit solution that allows an x-ray system user to use one or more earlier imaging media types in addition to the newer DR receiver panels.

In accordance with one embodiment, the present invention can provide a method for obtaining an image by using a digital radiography receiver in an x-ray imaging system of a type configured for film or computed radiography, where the x-ray imaging system including a manual operator control for generating at least an expose signal and a generator interface channel for transmitting the expose signal to an x-ray generator of the x-ray imaging system, the method can include providing a retrofit connection apparatus that adapts the x-ray imaging system for use with the digital radiography (DR) receiver by forming a receiver interface channel for communicating signals to and from the DR receiver, and providing an operator actuated switch cover for at least an expose operator action of the manual operator control, where in response to an operator control actuation for generating the expose signal by the expose operator action of the manual operator control, the operator actuated switch cover is configured to resist the generation of the expose signal by the expose operator action of the manual operator control until a reset of the DR receiver is initiated and acknowledged over the receiver interface channel, and transmitting the expose signal to the x-ray generator over the generator interface channel responsive to the expose operator action of the manual operator control passed through the operator actuated switch cover.

In accordance with one embodiment, the present invention can provide an apparatus configured to use a digital radiography receiver in an x-ray imaging system of a type configured for film or computed radiography, that can include a generator interface channel to communicate with an x-ray system of an x-ray imaging system, a manual operator control to generate at least a first, preparation signal and a second, expose signal, an interface component installed as a retrofit to the x-ray imaging system, the interface component including an operator actuated switch cover for at least an expose operator action of the manual operator control, and a receiver interface channel to communicate with a digital radiography receiver, where in response to an operator actuation to generate the expose signal by the expose operator action of the manual operator control, the operator actuated switch cover is configured to resist the generation of the expose signal by the expose operator action of the manual operator control until a reset of the DR receiver is initiated and acknowledged over the receiver interface channel.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings.

The elements of the drawings are not necessarily to scale relative to each other.

FIG. 2A and FIG. 2B are diagrams that illustrate another exemplary embodiment of a retrofit mechanism according to the application.

FIG. 5 is a diagram that illustrates a single, dual position, Prep and Expose button for use with existing x-ray system installations.

DESCRIPTION OF EXEMPLARY EMBODIMENTS

Figure 1A:
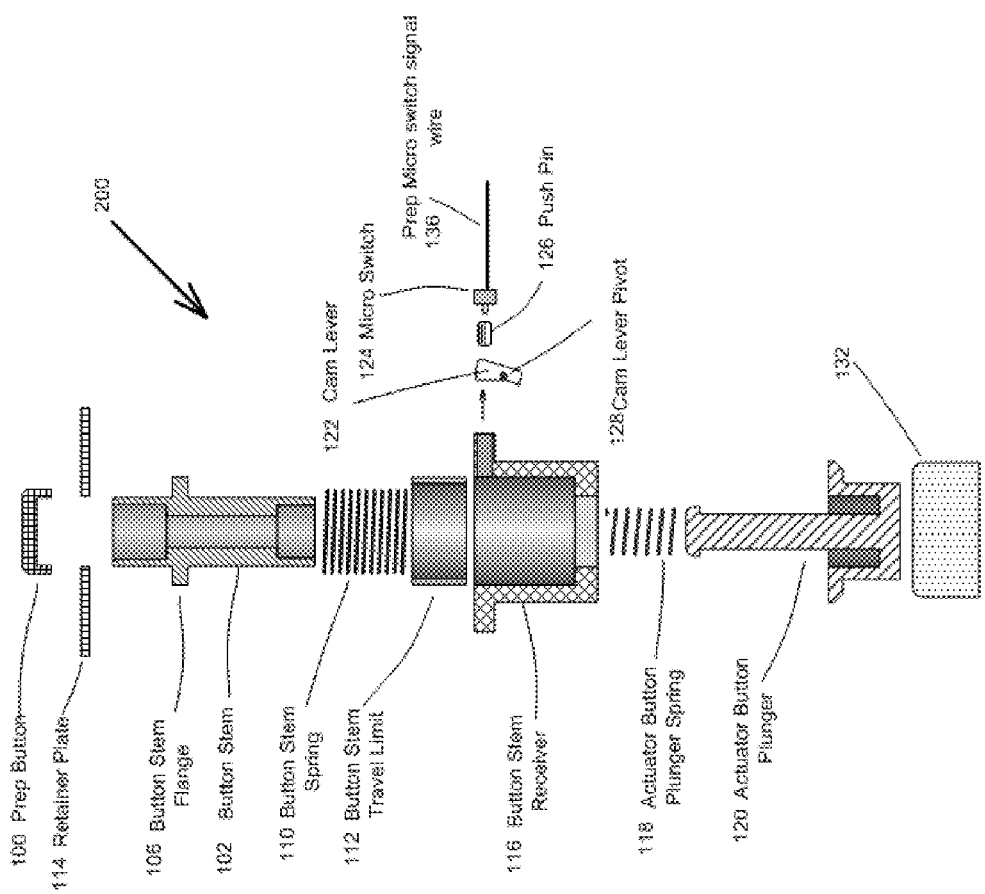
FIG. 1A and FIG. 1B are diagrams that illustrate an exemplary embodiment of a retrofit mechanism according to the application.

The following is a description of exemplary embodiments of the invention, examples of which are illustrated in the accompanying drawings. Wherever possible, the same reference numbers will be used throughout the drawings to refer to the same or like parts.

For simplicity and illustrative purposes, principles of the invention are described herein by referring mainly to exemplary embodiments thereof. However, one of ordinary skill in the art would readily recognize that the same principles are equally applicable to, and can be implemented in, all types of radiographic imaging arrays, various types of radiographic imaging apparatus and/or methods for using the same and that any such variations do not depart from the true spirit and scope of the application. Moreover, in the following description, references are made to the accompanying figures, which illustrate specific exemplary embodiments. Electrical, mechanical, logical and structural changes can be made to the embodiments without departing from the spirit and scope of the invention. In addition, while a feature of the invention may have been disclosed with respect to only one of several implementations/embodiments, such feature can be combined with one or more other features of other implementations/embodiments as can be desired and/or advantageous for any given or identifiable function. The following description is, therefore, not to be taken in a limiting sense and the scope of the invention is defined by the appended claims and their equivalents.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. Where they are used, the terms "first", "second", and so on, do not necessarily denote any ordinal or priority relation, but may be used for more clearly distinguishing one element or time interval from another.

Retrofitting a DR detector system into existing x-ray system hardware can be problematic because of strict regulatory requirements imposed on x-ray equipment, for example, when there is a possibility of exposing patients and/or operators to unintentional x-rays from malfunctioning equipment.

Further, the manufacturer of equipment used in an existing x-ray installation can be different than the manufacturer of a retrofittable DR detector designed to be incorporated into an existing x-ray installation. Accordingly, there exists the circumstance that an original manufacturer can void safety certifications for the original manufactured equipment when the original equipment has been found to have been invasively tampered with or when third party or foreign equipment (e.g., different manufacturing source) has been added. Voided safety certifications can be justified because the original manufacturer cannot guarantee the operational reliability of third party equipment, for example, with respect to patient and/or operator safety. Operation of an existing x-ray system hardware configuration without the needed safety certifications may violate government regulatory requirements (e.g., local, state, national) and/or make difficult the use of any new retrofit DR detector configured equipment.

Thus, testing and re-certification of a new hardware configuration including the original equipment may need to be completed before the configuration could be used for any diagnostic x-ray imaging. The added cost, both in time and money, of a re-certification process can be prohibitive and/or make the prospect of adding a retrofittable DR detector to an existing x-ray imaging system (e.g., film-based or CR) unattractive. It is therefore beneficial or imperative that noninvasive methods/apparatus for inserting retrofittable DR detector hardware into existing x-ray system hardware installations be devised that does not create a re-certification event(s) such as potential fault conditions that can expose patients and/or operators to unintended ionizing radiation.

A DR detector system retrofitted to an existing x-ray system hardware installation can have the potential for exposing patients to unintended x-rays, for example, when the DR detector image acquisition process fails to produce an acceptable image (e.g., clinically acceptable) during an x-ray exposure. A failure of the DR detector because of an unacceptable image forces a second x-ray exposure (e.g., of a patient) in order to obtain an acceptable diagnostic image. Such a second exposure exposes the patient to a second dose of radiation, which is unacceptable.

A DR detector system usually cannot respond instantaneously to an image acquisition event and requires a latency period to finish various internal operations (e.g., initialize, complete a reset operation). Once reset, the DR detector can be ready to begin an image acquisition cycle and receive an x-ray exposure for producing a corresponding high quality diagnostic image.

Thus, image acquisition processes can fail if the retrofit DR detector is not operationally ready for an x-ray exposure (e.g., cycle, integration) when an x-ray exposure event occurs. When the DR detector is not operationally ready, an insufficient amount of the x-ray ionization energy (e.g., a portion or all) fails to be captured by the DR detector system resulting in an underexposed image. Preventing this type of fault condition from occurring can require methods/apparatus whereby a signal that fires an x-ray generator is time delayed or held off until the DR detector system is operationally ready for the ensuing x-ray exposure.

Figure 10:
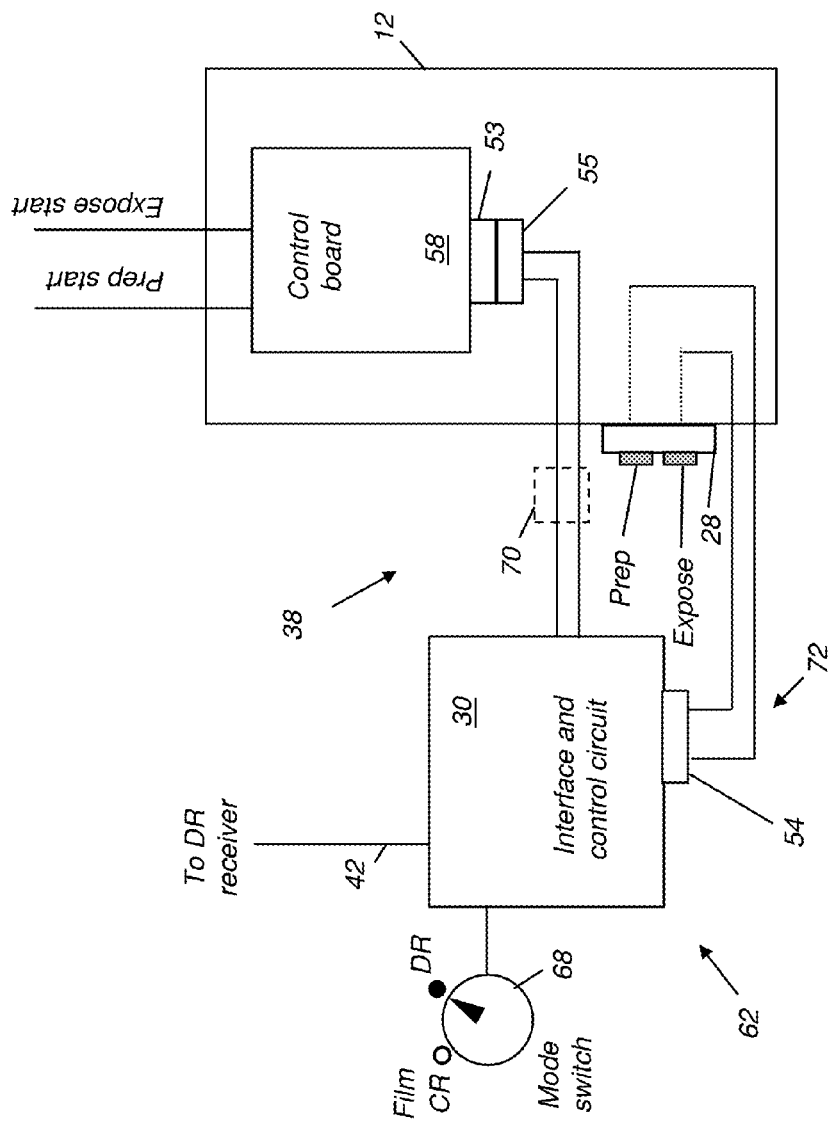
FIG. 10 is a schematic block diagram of an embodiment of a retrofit connection apparatus that uses panel-mounted or tethered switches of the existing imaging apparatus.

Delaying the x-ray generator expose signal can be accomplished by inserting an Interface and Control Circuit 30 as shown in FIG. 10 (i.e., FIG. 5B of U.S. Pat. No. 7,844,031). The disclosure of U.S. Pat. No. 7,844,031 is hereby incorporated herein in its entirety. As shown in FIG. 10, Interface and Control Circuit 30 breaks into the signal generating channel of the existing x-ray system hardware installation by disconnecting the Prep and Expose switch 28 and rerouting these signals to the control circuit 30. The modification shown in FIG. 10 is readily accomplished when the existing x-ray system hardware installation and associated connector apparatus 38 use conventional and easily obtainable connectors for connectors 53 and 55. In at least one instance, replacement operator control switches 28 or tethered operator control can be commercially purchased. However when a proprietary connector interface is employed, then invasive modification techniques can be required to obtain and reroute signals from Prep and Expose switches 28. Invasive modifications can be deemed unacceptable by the manufacturer of the existing x-ray system hardware (e.g., or the certifying authority), particularly when the invasive modifications involved cutting, disconnecting or rerouting existing signal cabling.

Referring to one embodiment of a retrofit apparatus 62 in FIG. 10, switch 28 of the original system is used with the retrofit connection of connector apparatus 38. Connector 54 is removed from connector 53 on control board 58 and re-connected to interface and control circuit 30 to form operator interface channel 72. Interface and control circuit 30 then uses timing as discussed with regard to FIG. 15 and conditions the signals from switch 28 on operator interface channel 72 to provide the needed delay and provides the conditioned signals over generator interface channel 70 at a connector 55 to control board 58. Switch 28 in such an embodiment may be panel-mounted or tethered. In one embodiment, connector 53 is externally mounted as a jack or plug for tethered switch 28 connection, making it particularly straightforward to provide the retrofit arrangement of connection apparatus 38. Still referring to FIG. 10, an optional mode selector 68 is provided for interface control circuit 30 in one embodiment. Mode selector 68 can be used to specify operation of control logic in interface and control circuit 30, in order to enable either the signal timing of a first mode (e.g., original or non-delayed timing) when removable media (film or CR cassette) is used or the signal timing of a second mode shown in FIG. 15 when a DR receiver panel is used.

Figure 11:
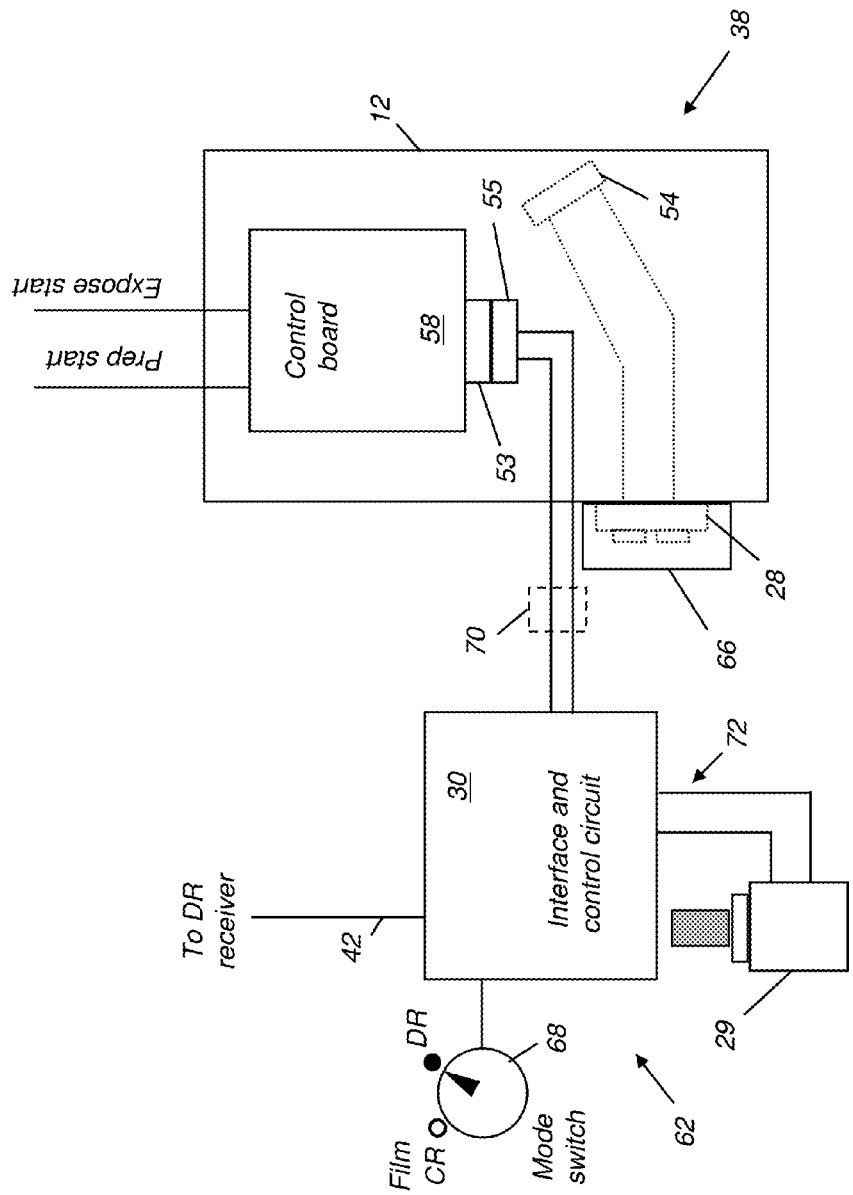
FIG. 11 is a schematic block diagram of an embodiment of a retrofit connection apparatus that uses a separate external switch and disables the existing switch for Prep and Expose functions of the apparatus of FIG. 5B.
Figure 12:
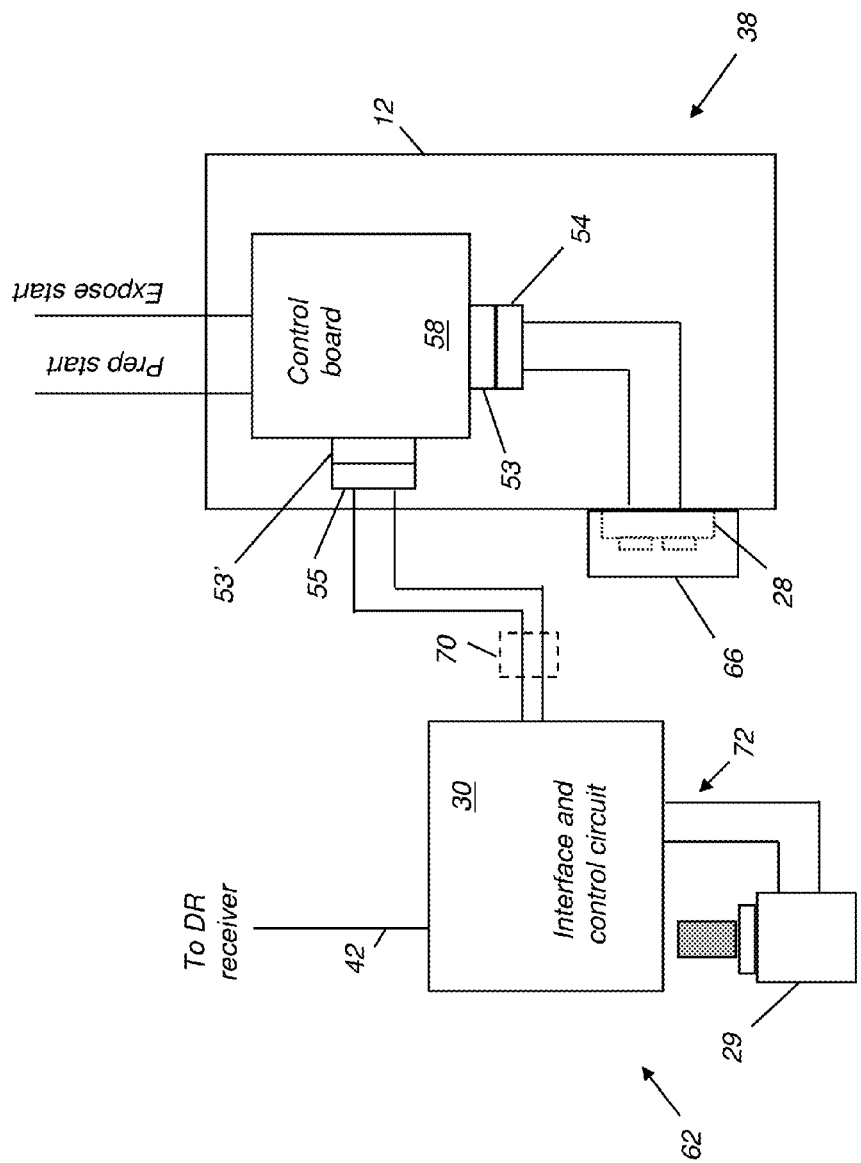
FIG. 12 is a schematic block diagram of an alternate embodiment for a retrofit connection apparatus that has connection to both existing and retrofit Prep and Expose switches.

Alternate embodiments as described in U.S. Pat. No. 7,844,031 are shown in FIGS. 11-12 (i.e., FIGS. 5C and 5D of U.S. Pat. No. 7,844,031). As shown in FIG. 11, Prep and Expose switch 28 of an existing x-ray system hardware installation can be disconnected and deactivated and replaced with a tethered hand switch that can serve as the new source for Prep and Expose signals (e.g., control switch 29) initiated by an operator. Here, connector 54 is disconnected from control board 58 or otherwise bypassed, and a cover 66 is applied over switches 28, controlling when, if ever, these switches are seen and/or used. As shown in FIG. 12, an alternative embodiment where connector 55 can be connected to connector 53', which can be implemented in addition to existing original connectors 53, 54 when such an option is available.

As shown in the embodiments of FIGS. 10 through 12, modifications to an existing x-ray installation allow Prep and Expose signals from switches 28 to be routed to or replaced and then intercepted by the Interface and Control Circuit 30 and to be conditioned through appropriated sequenced timing to guarantee that the x-ray generator Prep Start and Expose Start signals from operator console 12 are not asserted until after the DR detector or DR receiver has been reset and/or is ready for the image acquisition cycle using the DR receiver interface channel 42.

Figure 13:
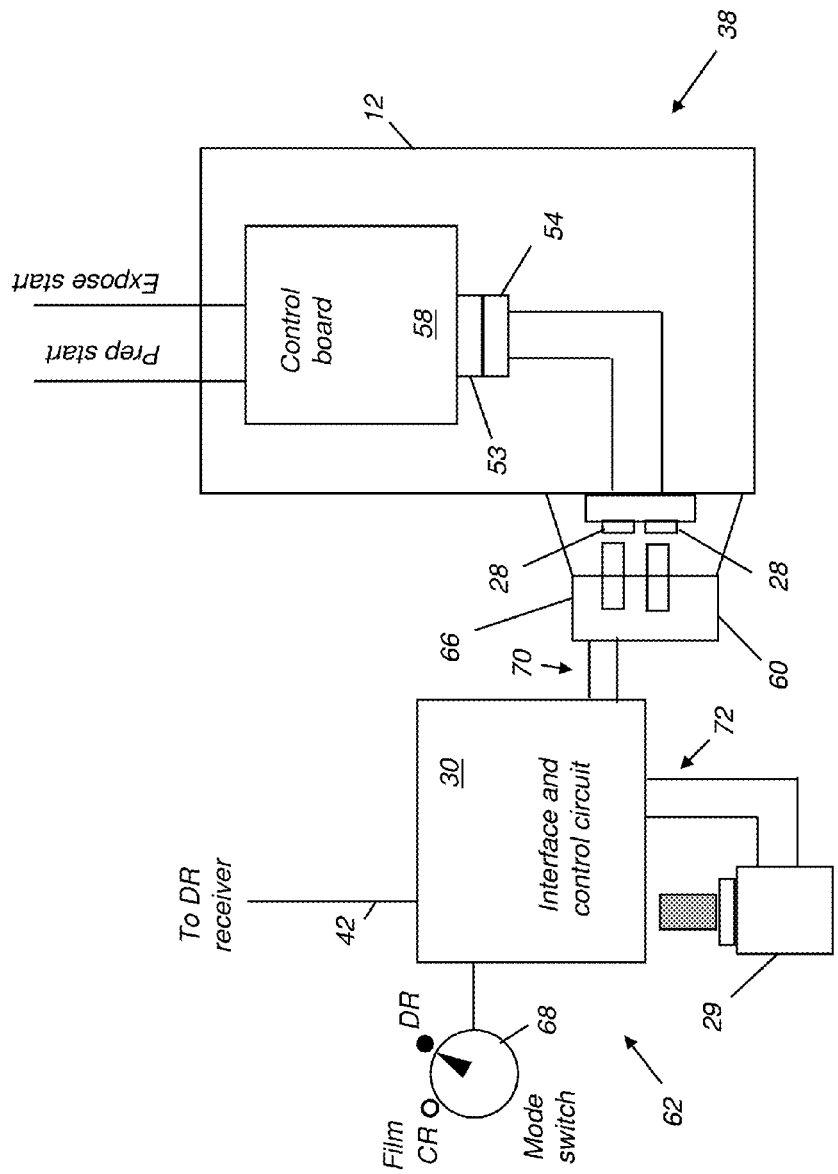
FIG. 13 is a schematic block diagram of an embodiment of a retrofit connection apparatus that mounts a separate switch controller on the operator control console.
Figure 14:
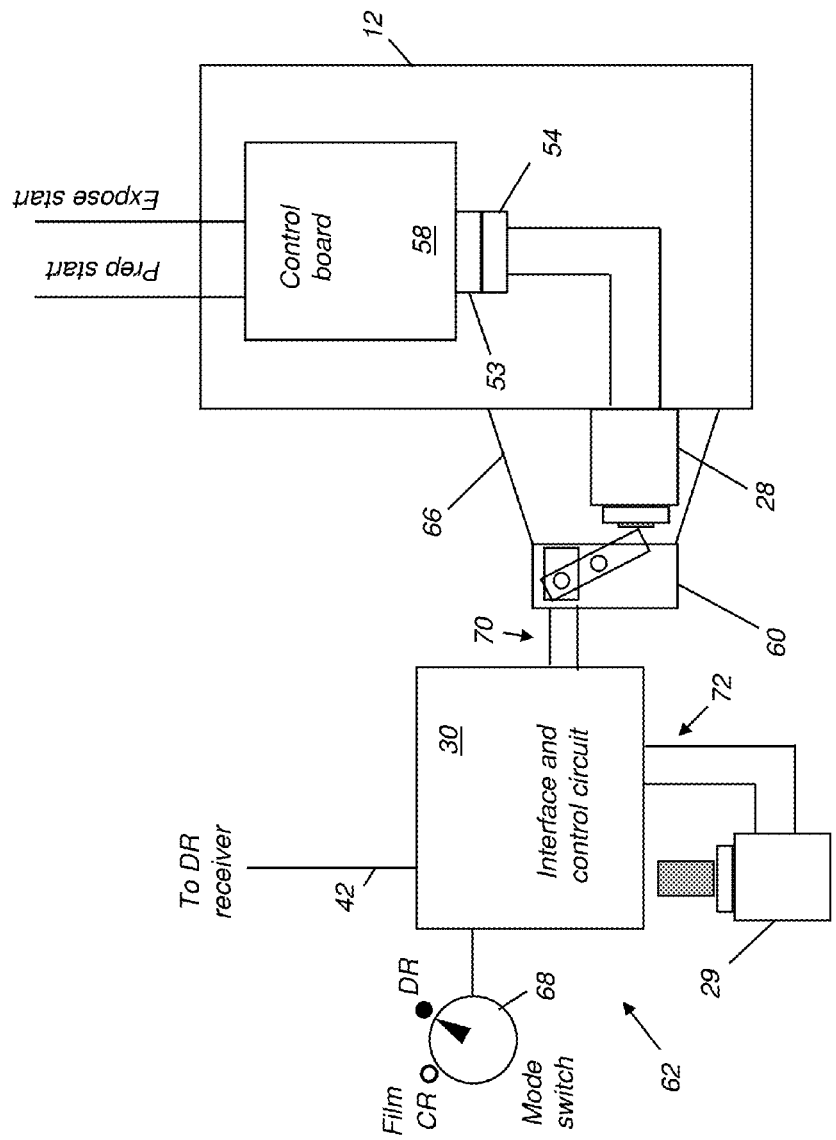
FIG. 14 is a schematic block diagram of an embodiment of a retrofit connection apparatus that mounts a separate switch controller on the operator control console for controlling a single two-position pushbutton.

There is the possibility that manufacturers of existing x-ray system hardware installations may object to modifications of the types shown in FIGS. 10 through 12 and remove certification of the altered equipment. Additional embodiments as described in U.S. Pat. No. 7,844,031 are shown in FIGS. 13-14 (i.e., FIGS. 5E and 5F of U.S. Pat. No. 7,844,031). Such non-invasive attempts to overcome any of these potential objections try interfacing to existing hardware using only an external mechanical interaction with existing push buttons switches 28 through switch controller 60. As shown in FIG. 13, activation of the Prep and Expose signals can be achieved by generating a mechanical force to push switch 28 in the same way as an operator's fingers. Exemplary mechanical force can be generated using commonly available mechanical actuators such as but not limited to linear solenoids, for example. When Interface and Control Circuit 30 receives Prep and Expose signals from operator control switch 29 and the DR detector has responded through DR receiver interface channel 42 by sending a reset confirmation message in FIG. 13, then the Interface and Control Circuit 30 can selectively send energization signals to switch controller 60 to activate operator control switch 28 thereby sending an output expose signal (Expose start) to the x-ray generator through Control Board 58. The timing diagram of FIG. 15 shows the sequence of Prep and Expose signals and related operations according to one DR retrofit embodiment.

Pressing the Expose switch sends a reset signal to the DR receiver panel. Reset of DR detector image-sensing circuitry typically takes no more than about 300 milliseconds, shown as time period D2 in FIG. 15. An optional acknowledgement signal is received from the DR receiver panel when reset has been completed. In one embodiment, the reset acknowledgement is required in order for x-rays to be generated and anode current is not provided until a positive acknowledgement of reset has been received back from the DR receiver panel. This helps to prevent exposing the patient to the x-ray radiation when the DR panel is not ready to form an image. Anode current that drives x-ray generation is provided for a period D3 that is usually no more than about 500 milliseconds. The integration period of the DR receiver panel is typically about 1 second and begins just before anode current is provided, extending past the time when anode current is stopped. In FIG. 15, period D1 is again caused by x-ray generator control circuitry and represents the timing interval between the time integration begins at the DR receiver panel and the time x-rays are emitted (anode current ON).

Figure 15:
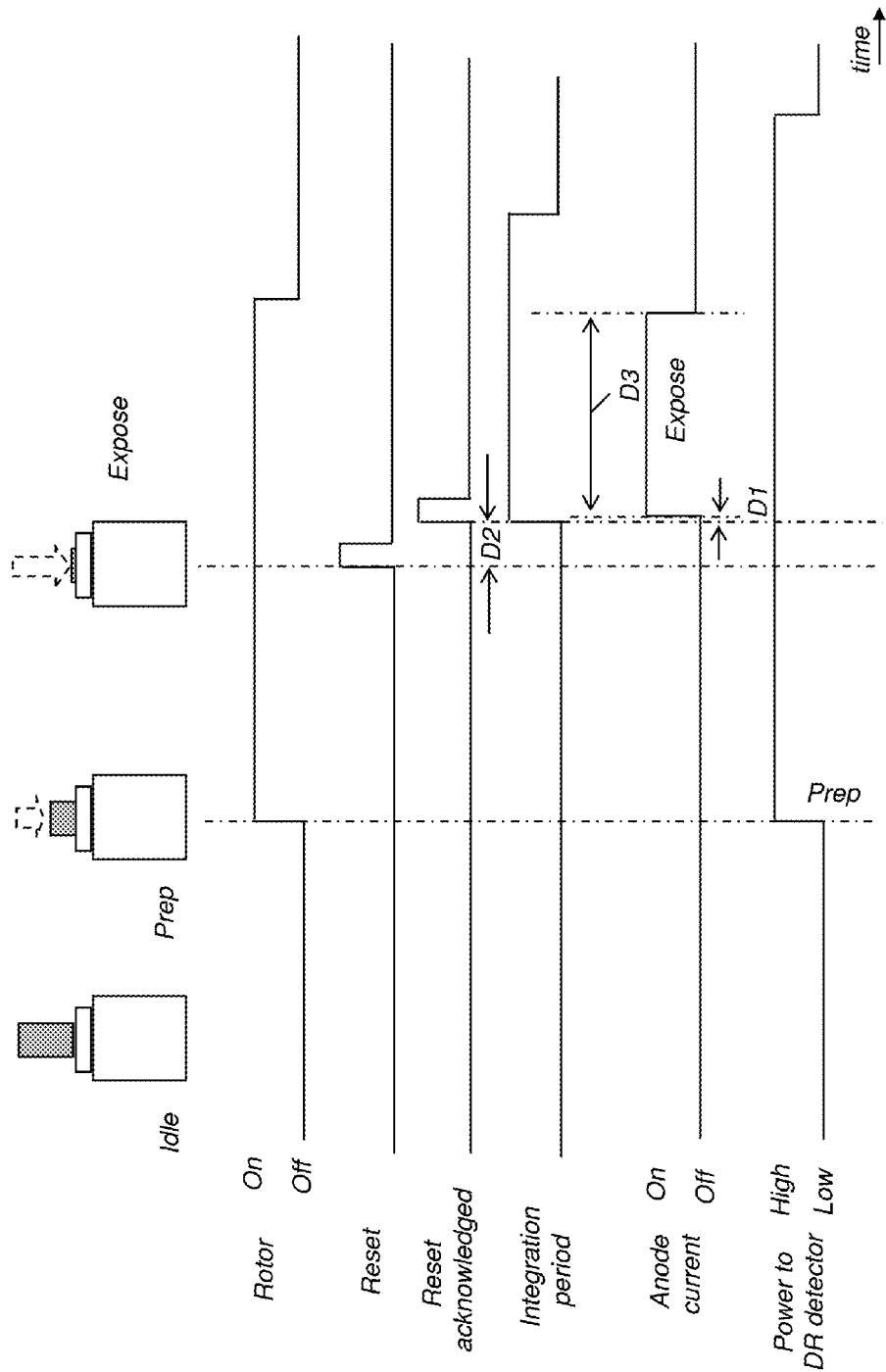
FIG. 15 is a diagram that shows timing states for conventional x-ray imaging system using a retrofit digital radiography detector embodiment.

It is noted that the timing diagram of FIG. 15 is exemplary and admits a number of modifications within the scope of the present invention. For example, the reset signal could alternately be provided from the moment the Prep switch is depressed, so that exposure and integration can begin more quickly following depressing the exposure switch. Delay time periods D1, D2, and D3 can vary in duration from those described. Timing, rather than positive reset acknowledgement, may be used to delay exposure (that is, with respect to FIG. 15, to delay anode current ON) for a brief period following selection by the operator in order to allow an interval for DR receiver panel reset before continuing. However, as noted earlier, requiring an actual acknowledgement of reset from the DR receiver panel itself may be more advantageous and may help to prevent wasted exposures where there is an equipment problem or communication difficulty.

Energization signals sent from Interface and Control Circuit 30 to the solenoids in switch controller 60 can be comprised of any of the known methods of solenoid energization such as relay contacts, bipolar or mosfet transistors for example.

Figure 16:
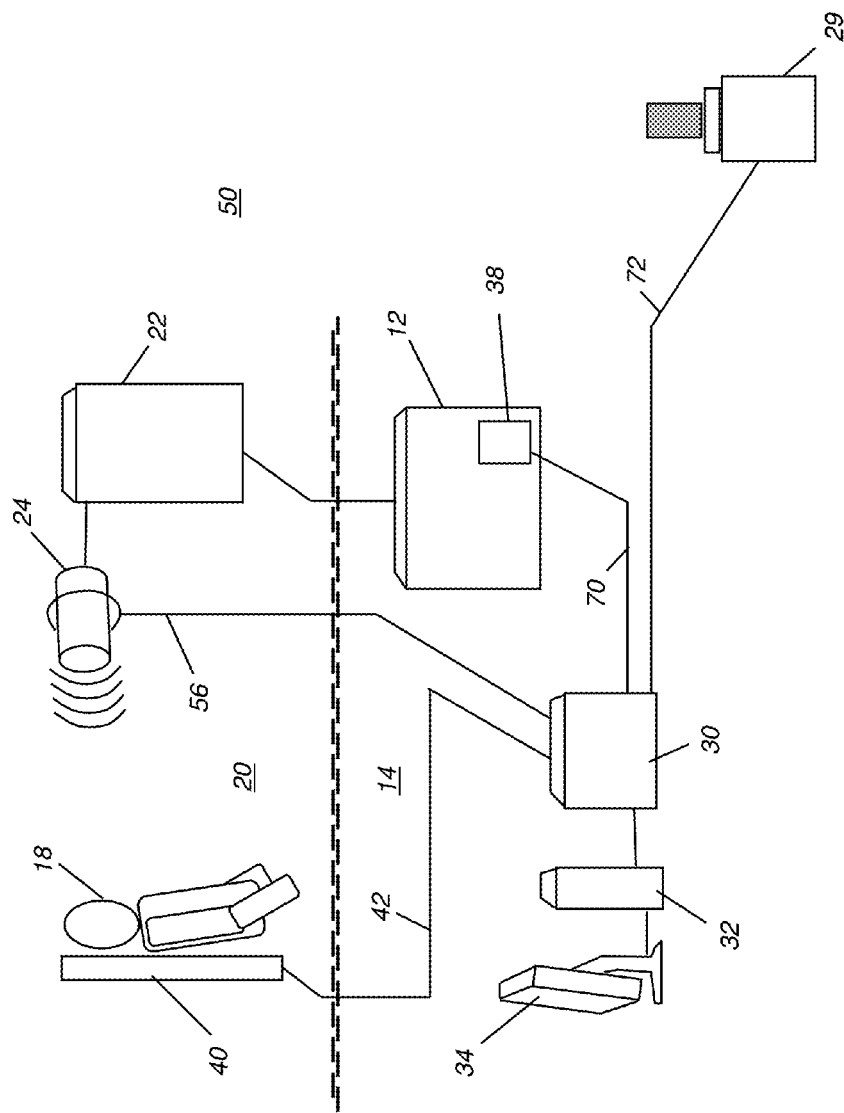
FIG. 16 is a schematic diagram showing an x-ray imaging system that has been retrofit according to one embodiment of the application.

The schematic diagram of FIG. 16 shows a retrofit imaging system 50 that substitutes a DR receiver panel 40 in place of a cassette and makes the necessary changes to x-ray exposure timing according to one embodiment of the application using wired connections. An x-ray generator 22 is installed in a radiation room 20, shown above the dashed line, where a patient 18 can be examined. An interface and control circuit 30 communicates between DR receiver panel 40 and other components of this system. Image data itself goes to an imaging processor 32, such as a computer or workstation that is in communication with a display 34. A generator interface channel 70 connects interface and control circuit 30 to operator control console 12 by means of a connection apparatus 38 for providing Prep and Expose signals with the appropriate timing. An operator control switch 29 is connected to interface and control circuit 30 by an operator interface channel 72 for operator control. Switch 29 may be a tethered switch as in FIG. 16 or may be configured to mechanically control existing switches mounted on control console 12. A DR receiver interface channel 42 is provided between DR receiver panel 40 and interface an control circuit 30 by an Ethernet cable connection or other type of high-speed data transfer link and may include other control signal lines for sending and receiving reset information and commands.

Figure 17:
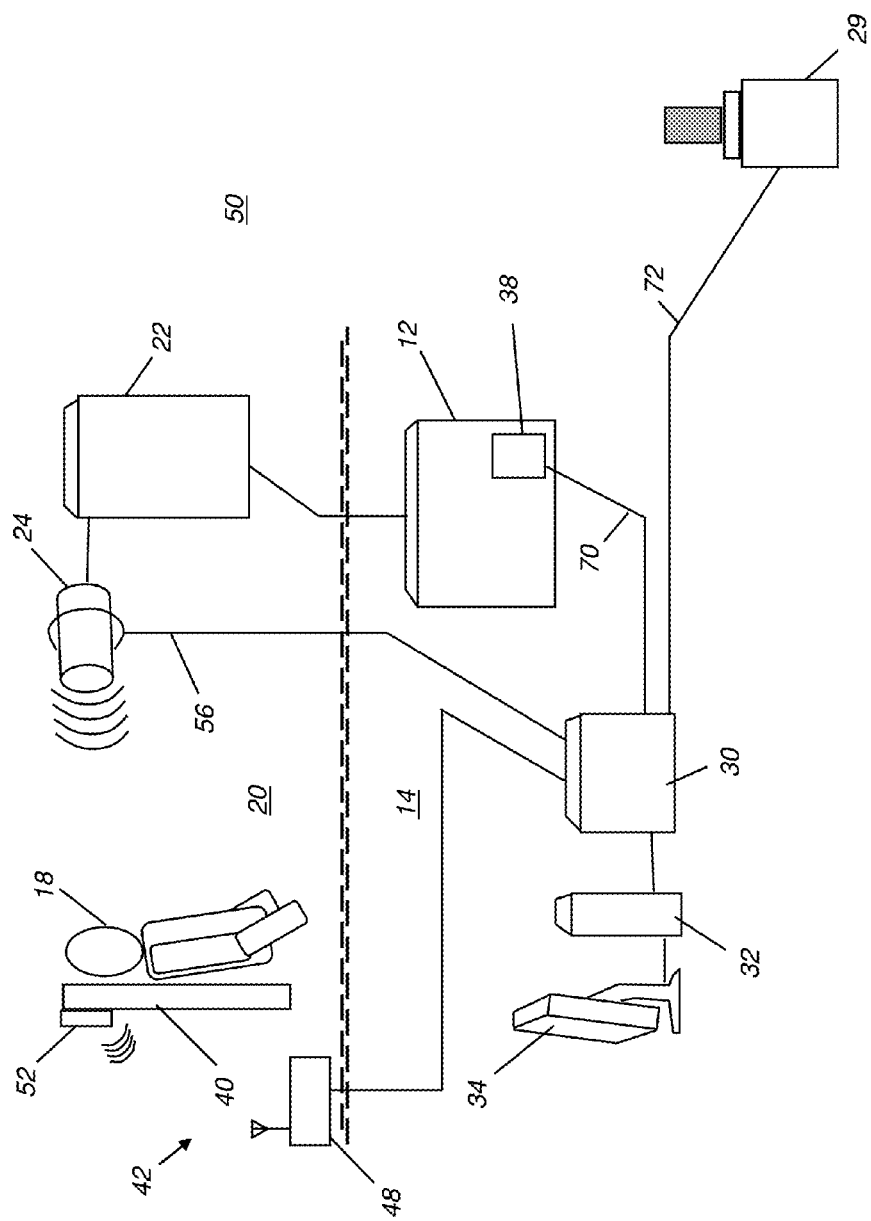
FIG. 17 is a schematic diagram showing a retrofit imaging system that has been retrofit according to a wireless embodiment of the application.

The schematic diagram of FIG. 17 shows retrofit imaging system 50 in an alternate, un-tethered embodiment. Here, a wireless communications link is provided for receiver interface channel 42 between DR receiver panel 40 and interface and control circuit 30. A transceiver 52 is connected to or provided as part of DR receiver panel 40 and communicates with a transceiver 48 that is connected to or provided as part of interface and control circuit 30. In one embodiment, battery power is also provided within DR receiver panel 40, so that no external wiring is required to the panel for operation. In another embodiment, only a power cord connection to DR receiver panel 40 is needed; the transmission channel to interface and control circuit 30 is wireless.

FIGS. 16-17 also show an optional sensor 56 for detecting a level of anode current that indicates active x-ray emission from x-ray tube 24. Anode current sensing by sensor 56 can be used to indicate that signal integration at DR receiver panel 12 should be terminated. It should be observed that the use of this additional sensor can also be done in a non-invasive manner and may therefore be preferable to other methods such as detecting or interrupting a termination signal from an AEC device, as described earlier, for example.

FIGS. 10-13 can provide apparatus or methods for preventing the assertion of an output expose signal to an x-ray generator before the DR detector has been reset and is ready to receive an x-ray image. Thus, a failed x-ray image acquisition process can not occur and the patient undergoing an x-ray diagnostic imaging procedure will not be needlessly exposed to harmful ionizing radiation.

However, even for the non invasive interface to existing x-ray system hardware of FIG. 13, objections can still be raised that there is a possibility of unintended x-ray exposure when a fault condition occurs in either the hardware or software of Interface and Control Circuit 30. Since the solenoid actuators of switch controller 60 in FIG. 13 are actuated by energization signals from Interface and Control Circuit 30, a failure in a component such as a mosfet transistor or a failure of control software used in the Interface and Control Circuit 30 could initiate an inadvertent (e.g., improper) actuation of solenoids in switch controller 60 even though the operator control switch 29 was not pressed. Such improper actuations can result in an unintended x-ray exposure of either the patient or an operator or both. Such a fault may be cited by the original manufacturer of the existing x-ray system hardware installation or certification authority as a failure mode that the original equipment was not designed to handle and the manufacturer or certifier is no longer able certify the reliability and safety of the equipment with the attachment of the additional or third party equipment (e.g., DR retrofit).

Exemplary embodiments of radiographic imaging methods and/or apparatus can retrofit an existing film-based or CR x-ray imaging apparatus to capture an x-ray image using a DR receiver. Certain exemplary embodiments can further remove or reduce the likelihood of inadvertent failure modes (e.g., described herein). Certain exemplary embodiments can provide a noninvasive implementation that can address at least the described inadvertent failure mode by removing the solenoid force input actuators and using the applied force of the operator's finger as the sole and exclusive source of actuation force.

Figure 1B:
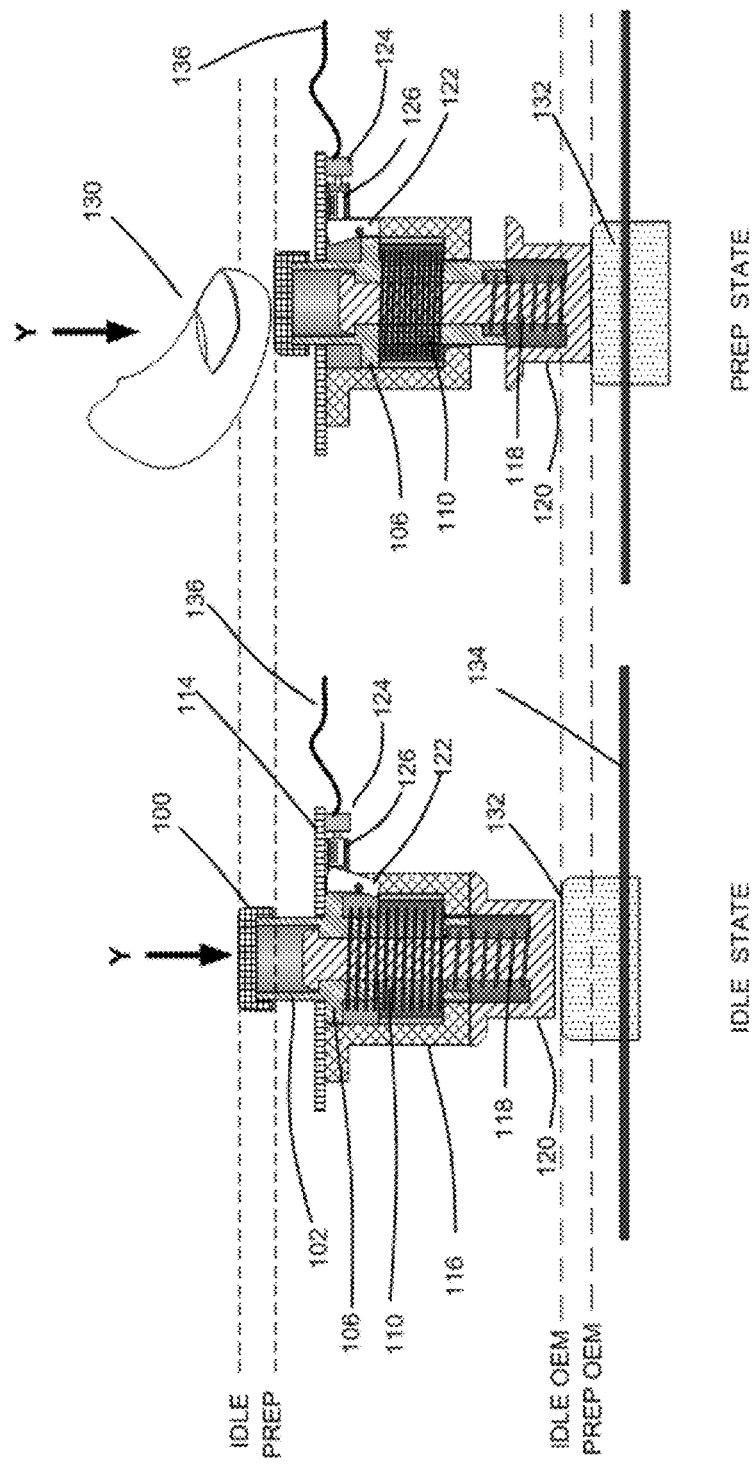

FIG. 1A and FIG. 1B are diagrams that illustrate an exemplary embodiment of a retrofit mechanism that can serve the purpose of interposing between a DR detector system and an existing x-ray system hardware installation (e.g., analog, film-based or CR). As shown in FIG. 1A and FIG. 1B, one retrofit embodiment can include a push button actuation mechanism for interfacing the Prep condition onto an existing x-ray hardware switch mechanism where the actuation mechanism requires and utilizes the active force or pressure of the operator's finger or thumb to generate the actuation force.

FIG. 1A shows an exemplary Prep Switch Interposer mechanism embodiment. Exemplary components of a Prep Switch Interposer mechanism 200 are shown in the exploded parts view of FIG. 1A. At the top of FIG. 1A, Prep Button 100 can serve as the force input and can be externally and physically accessible for the operator to push when a Prep state condition is to be initiated. Button stem 102 can attach to Prep Button 100 and transmit pressure from the operator's finger exerted at Prep Button 100. The output of Prep Switch Interposer mechanism 200 can be Actuator Button Plunger 120 at the bottom of FIG. 1A. The Actuator Button Plunger 120 can receive pressure from Button Stem 102 through Actuator Button Plunger Spring 118 and push the operatively adjacent existing x-ray hardware OEM Prep button 132 (e.g., beneath). The operator actuation force can be transmitted through one or more remaining switch components including Button Stem Spring 110, Button Stem Receiver 116 and Button Travel Limit 112.

As shown in FIG. 1A, when Button Stem 102 is pressed downward its flange portion 106 can compress Button Stem Spring 110 until Button Stem Flange presses against Button Stem Travel Limit 112. The Button Stem Travel Limit 112 can operate to limit the excursion of Button Stem 102 when the Button Stem 102 and Button Stem Flange 106 travel down through Button Stem Receiver 116, which can operate to contain and guide these components. A retainer plate 114 can be between the Prep Button 100 and the Button Stem Flange 106.

Button Stem Flange 106 can move down to displace Cam Lever 122 in a rotary fashion (e.g., counterclockwise), around Cam Lever Pivot 128 that can cause Push Pin 126 to move laterally to de-actuate Prep Micro Switch 124. In this way, a button push event initiated by the operator can be sensed and provided as a signal to the DR detector system to indicate the state of the external Prep button 100. Micro Switch 124 can be either of a type that is Normally Closed or Normally Open to facilitate the interface to the DR detector system. For example, the electrical state of Micro Switch 124 can be connected out to the DR detector system through Micro Switch wire 136. Alternatively, the electrical state and additional information can be wirelessly transmitted (e.g., to the DR detector system). As shown in FIG. 1A, there is no actuator mechanism that directly presses OEM Prep Button 132. The force of pressure on OEM Prep Button 132 is preferably and can be generated exclusively by the applied pressure of the operator's finger, which is further illustrated in FIG. 1B.

FIG. 1B shows Prep Switch Interposer mechanism 200 as an integrated assembly for two defined states: an IDLE STATE or not pressed condition and a PREP STATE or pressed condition. Exemplary positional limits for the switch input part Prep Button 100 and the output OEM Prep Button 132 are shown by the appropriately labeled horizontal dashed lines in FIG. 1B.

As shown in FIG. 1B, pressure from Operator finger 130 pressing in direction Y can cause Prep Button 100 to depress and force Actuator Button Plunger 120 to press down existing x-ray hardware OEM Prep button 132, which can be mounted beneath. At this position of Button Stem 102, Cam Lever 122 has rotated to shift Push Pin 126 away and to deactivate Micro Switch 124 thereby sending an actuation signal through Micro Switch wire 136. Actuator Button Plunger Spring 118 compresses to some degree to absorb force from Plunger 120 in case hardware OEM Prep button 132 hits any mechanical limit. Beneficially, the embodiment shown in FIG. 5 can not accidentally actuate existing x-ray hardware OEM Prep button 132 without the direct applied force from the operator's finger.

Figure 2B:
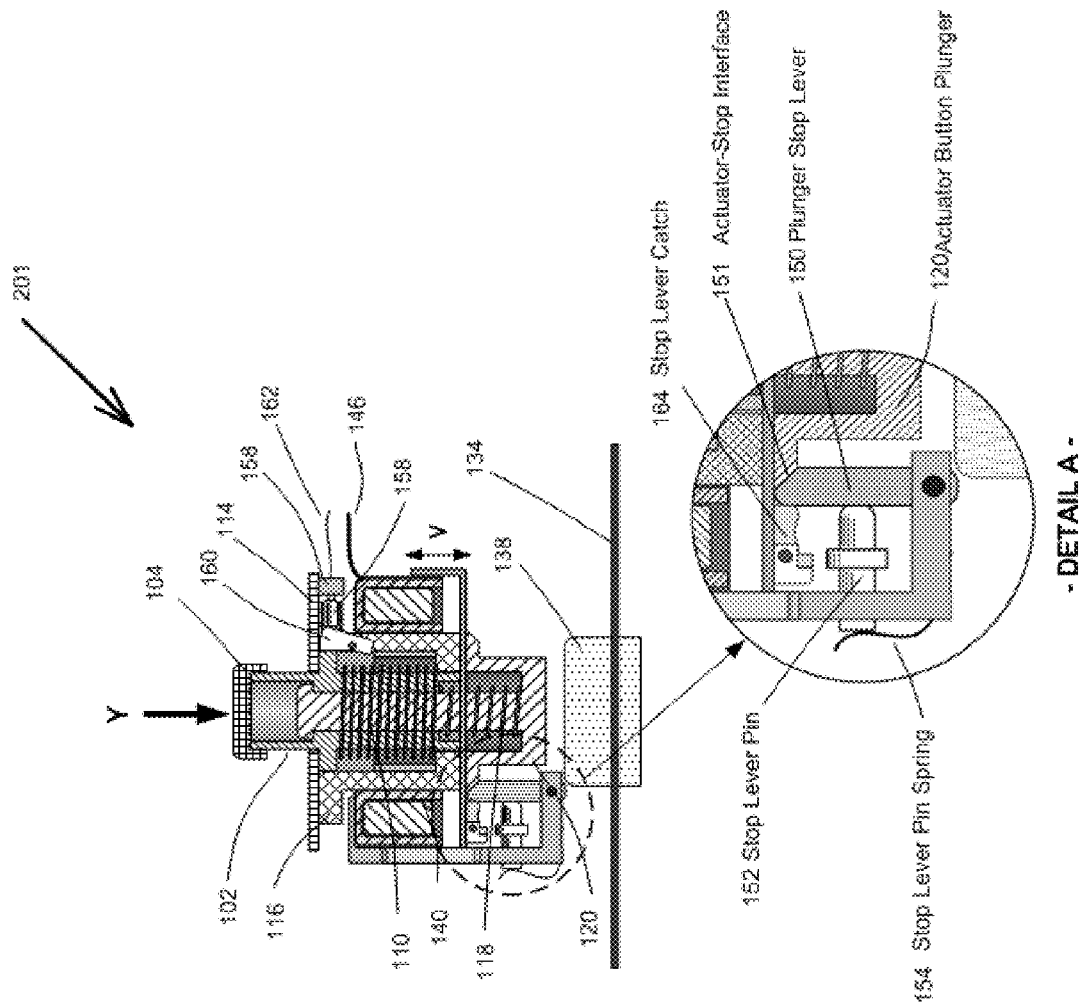

FIG. 2A and FIG. 2B are diagrams that illustrate an exemplary embodiment of a retrofit mechanism that can serve the purpose of interposing between a DR detector system and an existing x-ray system hardware installation (e.g., analog, film-based or CR). FIG. 2A shows an exemplary Switch Interposer mechanism embodiment.

FIG. 2B shows an exemplary EXPOSE switch mechanism that can provide a lockout capability to assure that pressure from Operator finger 130 will not be applied to an existing x-ray hardware Expose button until after a lockout release signal can be received or applied to the EXPOSE switch mechanism. In one embodiment, a lockout release signal can originate from the DR detector system and can be issued only when the DR detector is ready to acquire an x-ray image. As shown in FIG. 2B, an EXPOSE switch mechanism can use part of a PREP switch mechanism shown in FIGS. 1A and 1B.

Expose Switch Interposer mechanism 201 shown in FIG. 2B can be similar to Prep Switch Interposer mechanism 200 but can include at least one additional Release Mechanism. An exemplary Solenoid Release Actuator 203 for the Release Mechanism is shown in FIG. 2A. Referring to FIG. 2A, a solenoid portion of the Solenoid Release Actuator 203 can include a magnetically permeable Housing 140 that can be, for example, toroidal in shape and into which a copper wire Coil 142 is wound. Toroidal Housing 140 can be fashioned with a central opening into which a switch mechanism such as Prep Switch Interposer mechanism 200 can be fitted. Housing 140 can include pole end pieces 140a. When an electrical current is passed through Coil Wires 146, a resulting magnetic field created by the current can pull Armature 144 up against Housing pole end pieces 140a in direction V. A restoring spring (not shown in FIG. 2A or 2B) can act to keep Armature 144 away from Housing 140 at a predefined distance when Coil 142 is not energized. Stop Lever Catch 164, described herein, can be attached to Armature 144.

Solenoid Mounted Bracket 148 can be an assembly of parts that can be attached (e.g., removably, integrally, permanently) to Housing 140 at equivalent Attachment Points 149. Solenoid Mounted Bracket 148 can include Plunger Stop Lever 150, Plunger Stop Lever Pivot 150a, Stop Lever Pin 152, and Stop Lever Pin Spring 154. Plunger Stop Lever 150 can rotate about Plunger Stop Lever Pivot 150a. However, Stop Lever Pin 152 in conjunction with Stop Lever Pin Spring 154, can apply a force in direction U to Plunger Stop Lever 150, which can force Plunger Stop Lever 150 against Actuator Button Plunger 120 as shown in Detail A of FIG. 2B.

FIG. 2B shows Expose Switch Interposer mechanism 201 and includes Detail A that shows an enlarged view of Actuator-Stop Interface 151 between Actuator Button Plunger 120 and Plunger Stop Lever 150. As shown in Detail A, Actuator Button Plunger 120 can be resisted or prevented from any downward excursion as long as Plunger Stop Lever 150 can remain in a prescribed orientation (e.g., the vertical orientation in FIG. 2B). Plunger Stop Lever 150 can be urged or spring loaded against Actuator Button Plunger 120 at Actuator-Stop Interface 151 by Stop Lever Pin 152 in conjunction with Stop Lever Pin Spring 154. The force from the spring force can be a restoring force only, and is preferably insufficient to prevent downward travel of Actuator Button Plunger 120. Additional components can hold or prevent Plunger Stop Lever 150 from retracting away from Actuator Button Plunger 120.

As shown in FIG. 2B, Stop Lever Catch 164 can provide a securing function to prevent Plunger Stop Lever 150 from retracting away from Actuator Button Plunger 120. When current is applied to Coil 142, Armature 144 can be magnetically attracted to Housing 140 and move vertically up until contacting to rest against Housing pole end pieces 140a. This action resulting from current applied to Coil 142, can retract Stop Lever Catch 164 (e.g., permanently attached to Armature 144) and allow Plunger Stop Lever 150 to rotate away from Actuator Button Plunger 120.

Expose Button 104 can force down Button Stem 102 to compress Button Stem Spring 110 whereby Cam Lever 160 can rotate and deactivate Micro Switch 158 to provide a signal to the DR detector system indicating the state of the external Expose Button 104 of the Expose Switch Interposer mechanism 201.

Figure 3A:
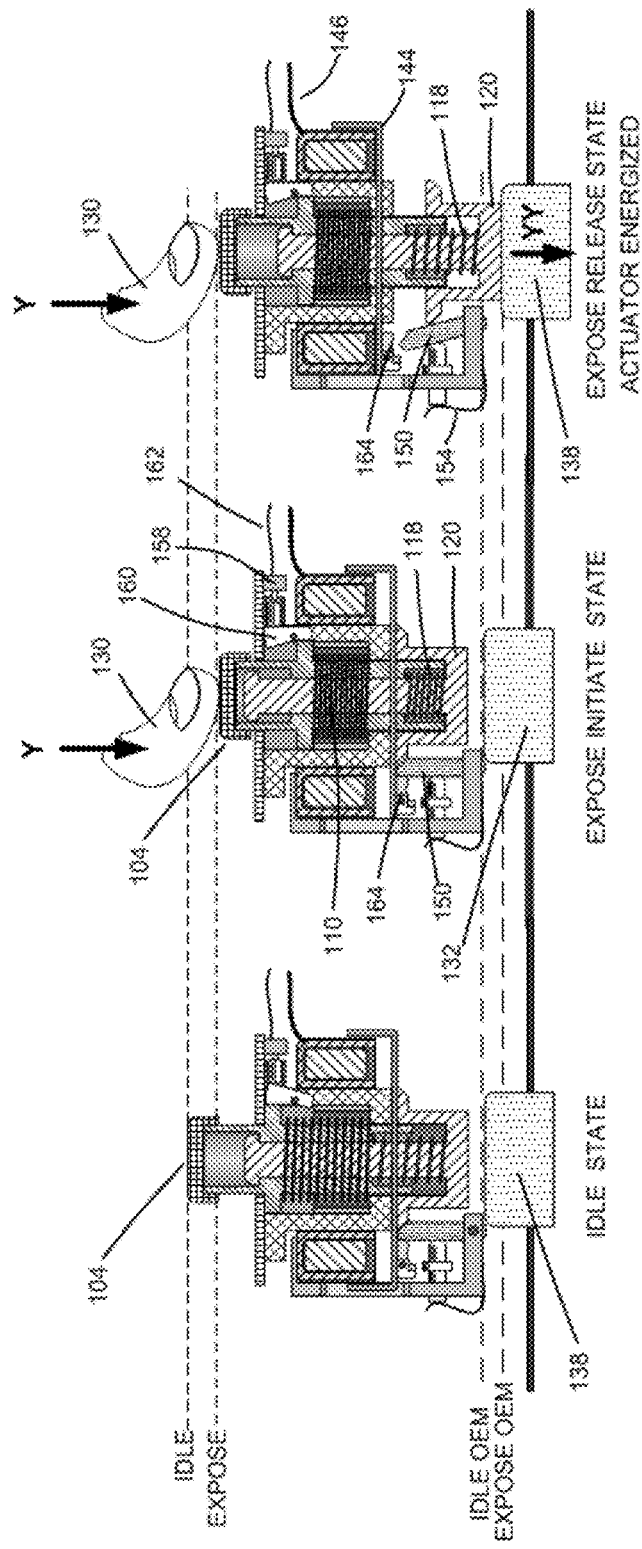
FIG. 3A and FIG. 3B are diagrams that illustrate an exemplary Expose sequence embodiment according to the application.

An exemplary Expose sequence embodiment will now be described with reference to FIG. 3A and FIG. 3B, although exemplary Expose sequence embodiments herein are not intended to be so limited. Three allowed states can be as follows: the IDLE STATE or unpressed condition, the EXPOSE INITIATE STATE or pressed but not released condition, and the EXPOSE RELEASE STATE where OEM Expose Button 138 is depressed as shown in FIG. 3A. The three allowed states can be implemented by Expose Switch Interposer mechanism 201. Exemplary positional limits for the switch input Expose Button 104 and the output OEM Expose Button 138 are shown by the appropriately labeled horizontal dashed lines in FIG. 3A.

As shown in FIG. 3A, the IDLE STATE can have input Expose Button 104 and output OEM Expose Button 138, each in a respective idle position. When the EXPOSE INITIATE STATE is desired, Operator finger 130 can press Expose Button 104 down in direction Y to the input Expose Button 104 EXPOSE position, which can compress Button Stem Spring 110 and Actuator Button Plunger Spring 118. The force of Actuator Button Plunger Spring 118 can load Actuator Button Plunger 120 against Plunger Stop Lever 150 that can operate to resist or prevent Actuator Button Plunger 120 from pressing output OEM Expose Button 138. In this way, a requested Expose condition (e.g., transmitted to the DR detector system via Expose switch signal wire 162) by the operator can be locked out (e.g., temporarily) to prevent the pressing of an existing x-ray system hardware button 138 until after the DR detector system is ready to receive an x-ray exposure.

When the DR detector has sent a reset confirmation message to Interface and Control Circuit 30, an energization signal can be sent (e.g., sequentially, concurrently) to Solenoid Release Actuator 203. The Expose Switch Interposer mechanism 201 can then enter the EXPOSE RELEASE STATE and Stop Lever Catch 164 can retract and allow Plunger Stop Lever 150 to swing away to release Actuator Button Plunger 120, which can then move freely to press output OEM Expose Button 138 in direction YY as shown.

Figure 3B:
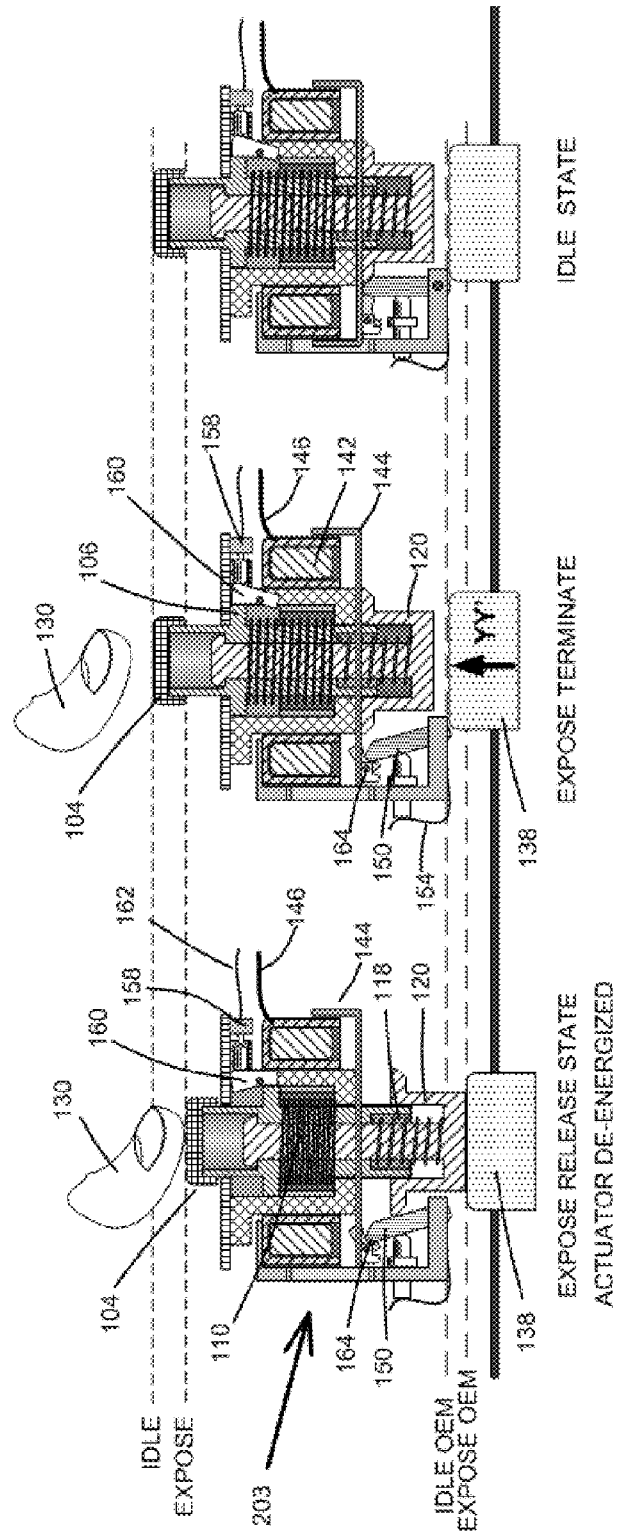

Three additional allowed states can be as follows: the ACTUATOR DE-ENERGIZED state, the EXPOSE TERMINATE state where operator finger pressure is removed from input Expose Button 104 and OEM Expose Button 138 is released and finally the return to the non-actuated IDLE STATE as shown in FIG. 3B. The three additional allowed states can be implemented by Expose Switch Interposer mechanism 201. Again, positional limits for the switch input Expose Button 104 and the output OEM Expose Button 138 are shown by the appropriately labeled horizontal dashed lines in FIG. 3B.

During an x-ray expose cycle, the operator preferably maintains pressure on input Expose Button 104 to continue the x-ray exposure. The ACTUATOR DE-ENERGIZED state can be entered after the EXPOSE RELEASE STATE shown in FIG. 3A when the Solenoid Release Actuator 203 is unlocked (e.g., de-energized), for example when the electrical current applied to Coil 142 is removed, which can allow Armature 144 to return to its non energized position as shown. Stop Lever Catch 164 is designed to pivot partially upward until contacting Plunger Stop Lever 150 to avoid interference. While pivoted partially upward, Plunger Stop Lever 150 can be free to pivot back to a vertical position from the urging of Stop Lever Pin Spring 154 as Actuator Button Plunger 120 retracts up to its idle position.

When Operator finger 130 removes pressure from Expose Button 104 after an x-ray expose cycle has terminated (e.g., or initiated), the EXPOSE TERMINATE state can be entered. Actuator Button Plunger 120 can return to the restored position where Actuator Button Plunger 120 no longer presses OEM Expose Button 138, which can then move in direction YY' to the IDLE OEM position. Button Stem Flange 106 can retract to force Expose Cam Lever 160 to actuate Expose Micro Switch 158 to signal the DR detector system (e.g., controller or application software) that Expose input Expose Button 104 is no longer depressed and in the IDLE STATE. In one embodiment, the drawing for the EXPOSE TERMINATE state shown in FIG. 3B is not accurate because Plunger Stop Lever 150 still rotated. In exemplary embodiments, Plunger Stop Lever 150 would have already returned to the position of the final IDLE STATE, but FIG. 3B is shown this way to facilitate discussion of exemplary expose sequence operations.

Benefits provided by Expose Button 201 embodiments include that an x-ray exposure cycle can only be initiated by force from Operator finger 130. Further, an x-ray exposure cycle by Expose Button 201 embodiments cannot be initiated by false energization of Solenoid Release Actuator 203 that might be caused by hardware or software system failure.

Figure 4A:
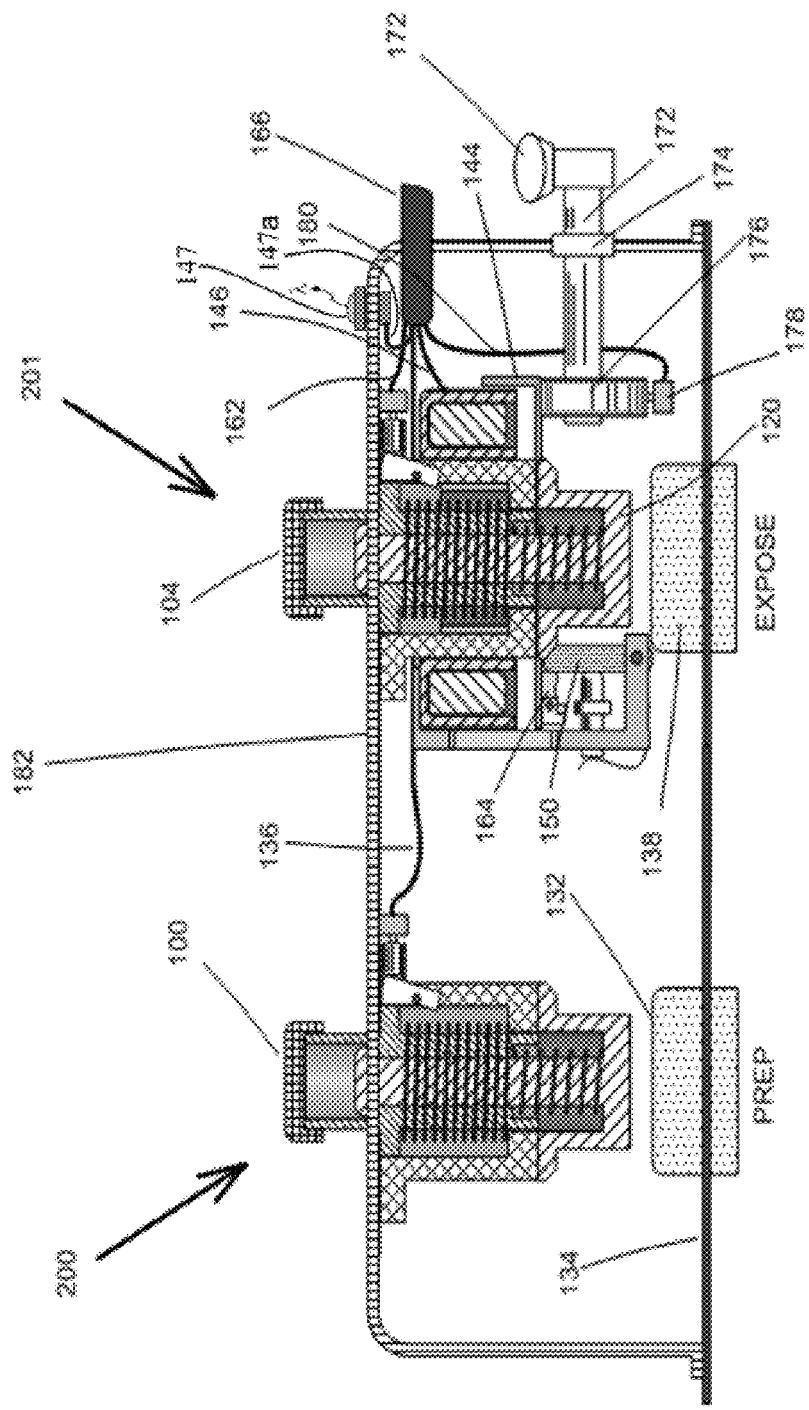
FIG. 4A shows Switch Assembly Housing 182 with Lockout Override Lever 172 in the override position.
Figure 4B:
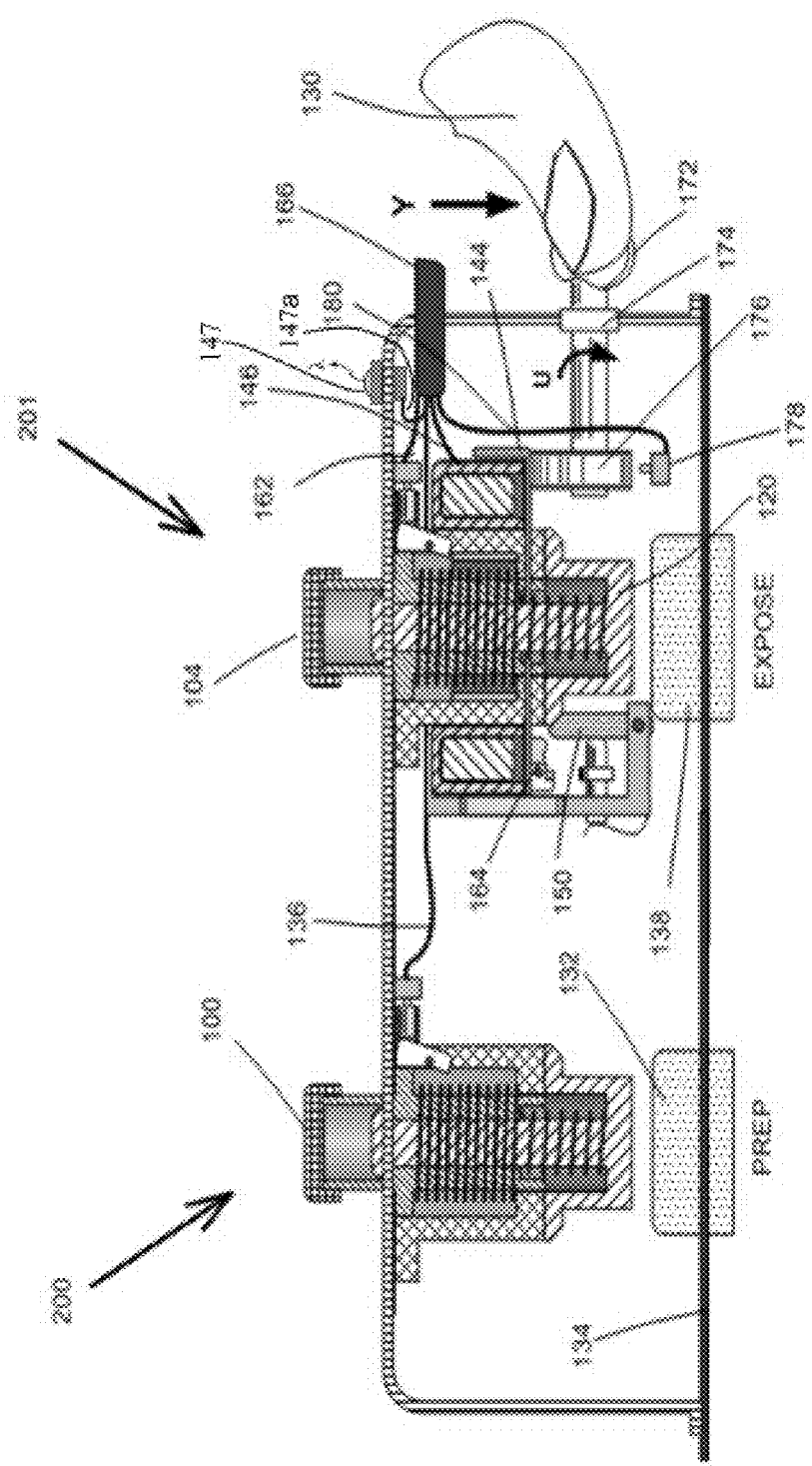
FIG. 4B shows Switch Assembly Housing 182 with Lockout Override Lever 172 in the override position.

FIG. 4A and FIG. 4B are diagrams that illustrate an exemplary embodiment of a retrofit mechanism that can serve the purpose of interposing between a DR detector system and an existing analog x-ray imaging system Prep Switch and Expose Switch installation. Prep Switch Interposer mechanism 200 and Expose Switch Interposer mechanism 201 can be assembled together into a composite unit to provide a non-invasive and/or fail-safe interface to an existing x-ray system installation where there is a dual button interface with both an OEM Prep button and an OEM Expose button. As shown in FIG. 4A, Switch Assembly Housing 182 can securely hold each Interposer mechanism 200, 201 and/or spatially position both to be oriented corresponding to (e.g., above) the OEM Prep and Expose buttons 132 and 138. For example, Switch Assembly Housing 182 can be securely fastened to OEM Console Top Cover 134. In exemplary embodiments, Switch Assembly Housing 182 can be permanently, removably, hingedly, or reciprocally between first and second positions as known to one skilled in the art.

In addition to the Prep Switch Interposer mechanism 200 and Expose Switch Interposer mechanism 201, an Expose Lockout Override function can be incorporated at the Switch Assembly Housing 182. In one embodiment, an Override mechanism can include: Lockout Override Lever 172, Lockout Override Bearing 174 and Lockout Override Cam 176.

One function of an Override mechanism is to provide a way for an operator to override or defeat the normal Expose Lockout capability of Expose Switch Interposer mechanism 201. In one embodiment, this can be accomplished by providing an alternate way to lift Armature 144 and Stop Lever Catch 164 to allow Plunger Stop Lever 150 to rotate out of the way of Actuator Button Plunger 120.

In addition, Lockout Override Switch 178 can be used to monitor the position of Lockout Override Cam 176 to provide a signal to the DR detector system indicating the state of the Lockout Override mechanism, which can be sent on change, at all times and/or intermittently. FIG. 4A shows Lockout Override Switch 178 in the actuated state. A signal from Lockout Override Switch 178 can be transmitted out (e.g., to the DR detector system) via Lockout Override Switch Wire 180 through Harness cable 166, which can also contain one or more of Coil wire 146, Expose Micro switch signal wire 162, and Prep Micro switch signal wire 136.

Overriding the Expose Lockout is a feature that can be used when an operator desires to return to a conventional x-ray exposure technique using CR imaging media or film imaging media. As shown in FIG. 4B, when Operator finger 130 presses down onto Lockout Override Lever 172, Lockout Override Cam 176 can be caused to rotate Lockout Override Bearing 174 in direction U that can lift Armature 144 and Stop Lever Catch 164 out of the way. Lifted Armature 144 and Stop Lever Catch 164 can permit an operator to be able to push Expose Button 104 and immediately depress OEM Expose Button 138 to trigger an x-ray exposure (e.g., using Actuator Button Plunger 120).

When Lockout Override Cam 176 is rotated as shown in FIG. 4B, Lockout Override Switch 178 can change its activation state and a signal indicating this change can be sent to the DR detector system. An activation state signal along with signals from Expose Micro switch signal wire 162 and Prep Micro switch signal wire 136 can provide state information, preferably on all physical inputs applied by an operator to an existing x-ray system, to the DR detector system. Lockout Override Lever 172 can include a restoring spring, which is not shown, which brings Lockout Override Lever 172 back to the non override position as shown in FIG. 4A, which can assure an Expose Lockout capability for Expose Switch Interposer mechanism 201 can be overridden only by direct operator action.

The lockout capability embodiment illustrated in FIG. 4A and FIG. 4B is not the only means to accomplish an Expose Lockout override function, but is provided to show one exemplary implementation.

Many existing x-ray system hardware installations make use of a single, dual position, Prep and Expose button instead of a two button interface. A single, dual position, Prep and Expose hand switch 202 is shown in FIG. 5. Switch components can include OEM Prep and Expose Button 190 that can sit atop OEM Switch Housing 192 and OEM Switch Cable 194 through which Prep and Expose signals are transmitted. The switch is shown in three different states that an operator can set, namely, IDLE, PREP and EXPOSE. The dashed lines show exemplary positional limits or positions of OEM Prep and Expose Button 190 for each of the OEM states.

Figure 6:
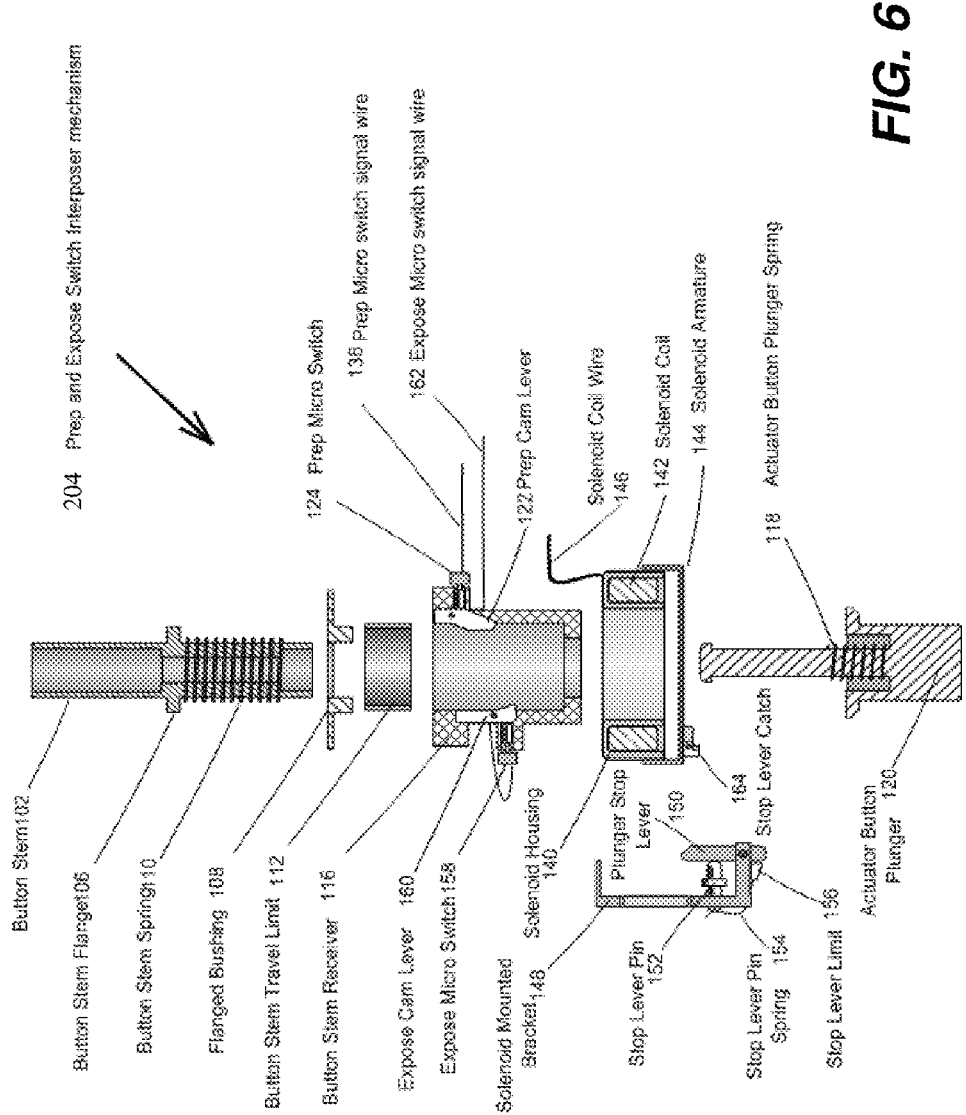
FIG. 6 is a diagram that illustrates yet another exemplary embodiment of a retrofit mechanism according to the application.

FIG. 6 is a diagram that illustrates an exemplary embodiment of a retrofit mechanism that can serve the purpose of interposing between a DR detector system and an existing analog x-ray imaging system Prep and Expose Switch installation. FIG. 6 shows Prep and Expose Switch Interposer mechanism 204 that can include a modified version of an Expose Switch Interposer mechanism 201. In one embodiment, parts making up Prep and Expose Switch Interposer mechanism 204 can include components of Expose Switch Interposer mechanism 201 with differences including Button Stem 102, Actuator Button Plunger 120 and Button Stem Spring 110 can be lengthened to provide the extra distance needed by a three state button. Further, Stop Lever Limit 156 can be added to prevent or resist Plunger Lever 150 from rotating beyond the vertical position by the applied force of Stop Lever Pin 152 and Stop Lever Pin Spring 154.

In addition, a second Micro switch can be added to account for the fact that both a Prep and Expose function are incorporated into a single mechanism. Prep Micro Switch 124 can be added adjacent Button Stem Receiver 116 along with associated Prep Cam Lever 122 and Prep Micro Switch signal wire 136. These exemplary components can provide a Prep state signal to the DR detector system when the Prep and Expose Switch Interposer mechanism 204 is set in a Prep state by an operator. In one embodiment, a second micro switch (e.g., Prep) can be optional. Expose Micro Switch 158 can be positioned adjacent Button Stem Receiver 116 offset (e.g., at a lower placement) from Prep Micro Switch 124. Expose Micro Switch 158, Expose Cam Lever 160 and Expose Micro Switch signal wire 162 serve the same purpose as or operate similar to Prep Micro Switch 124 except these components signal to the DR detector system when the Prep and Expose Switch Interposer mechanism 204 is in the Expose state. A Flanged Bushing 108 can be added near the Button Stem travel Limit 112.

Figure 7:
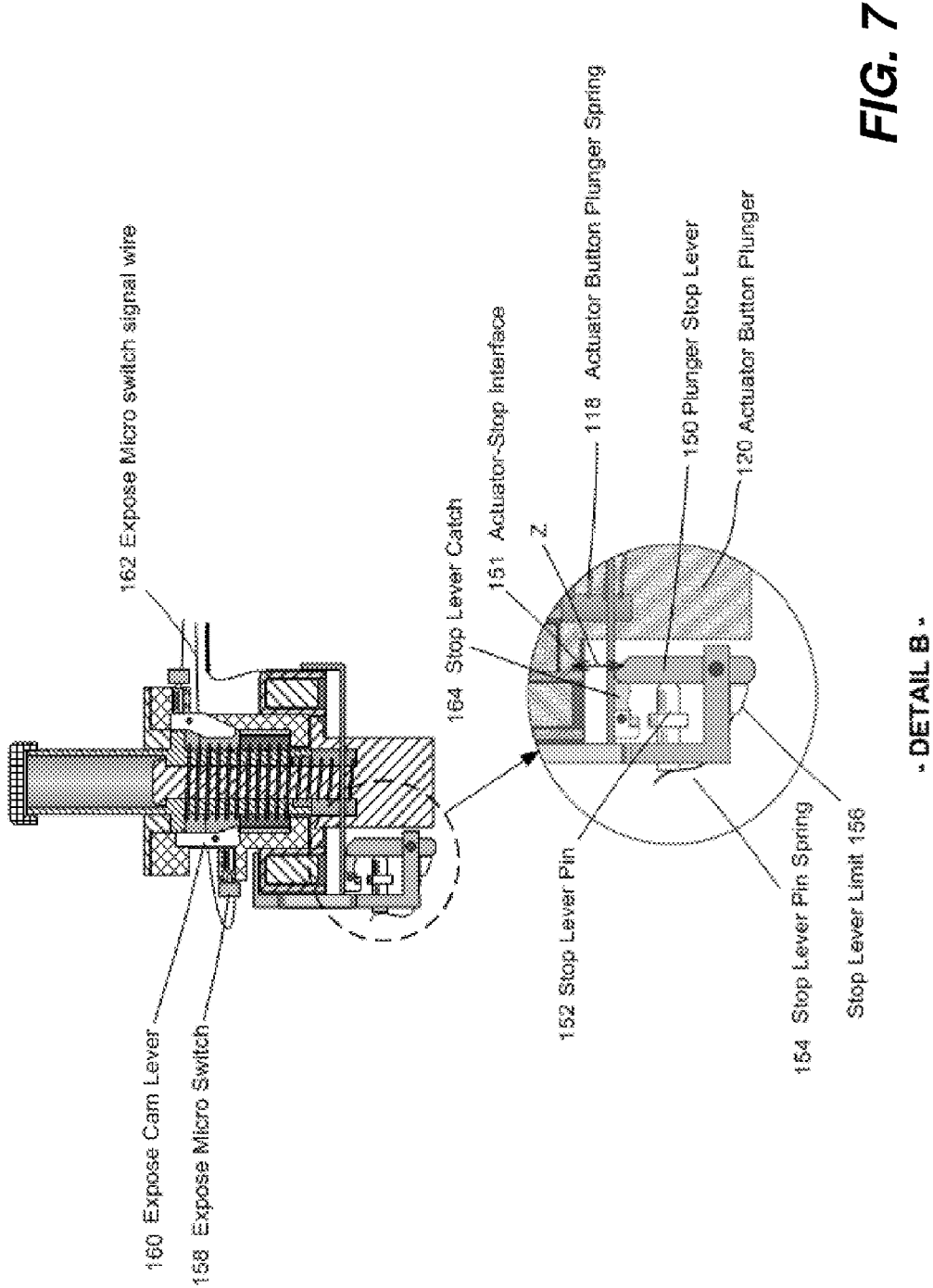
FIG. 7 is a diagram that illustrates an exemplary Prep and Expose Switch Interposer mechanism assembled.

The exemplary Prep and Expose Switch Interposer mechanism 204 is shown assembled in FIG. 7. The Prep and Expose Switch Interposer mechanism 204 is shown in the IDLE state where the input button (e.g., Prep and Expose Button 188) is not depressed in FIG. 7. As shown in DETAIL B of FIG. 7, changes with this configuration can include Plunger Stop Lever 150 may not touch Actuator Button Plunger 120 at the Actuator Stop Interface 151 when the switch is in the IDLE state. Accordingly, Stop Lever Limit 156 can be used to rotationally limit the excursion of Plunger Stop Lever 150. Extra space between Actuator Button Plunger 120 and Plunger Stop Lever 150 can provide an exemplary space or distance Z that can allow Actuator Button Plunger 120 to travel when a Prep state is applied by an operator so that the OEM button (e.g., OEM Prep and Expose Button 190) may be pressed and/or move to the PREP STATE position.

In certain exemplary embodiments, Prep and Expose Switch Interposer mechanism 204 can be configured to engage or have a prescribed spatial relationship to, surrounding a part of or on top of an OEM Prep and Expose Button (e.g., as shown in FIG. 5).

Figure 8:
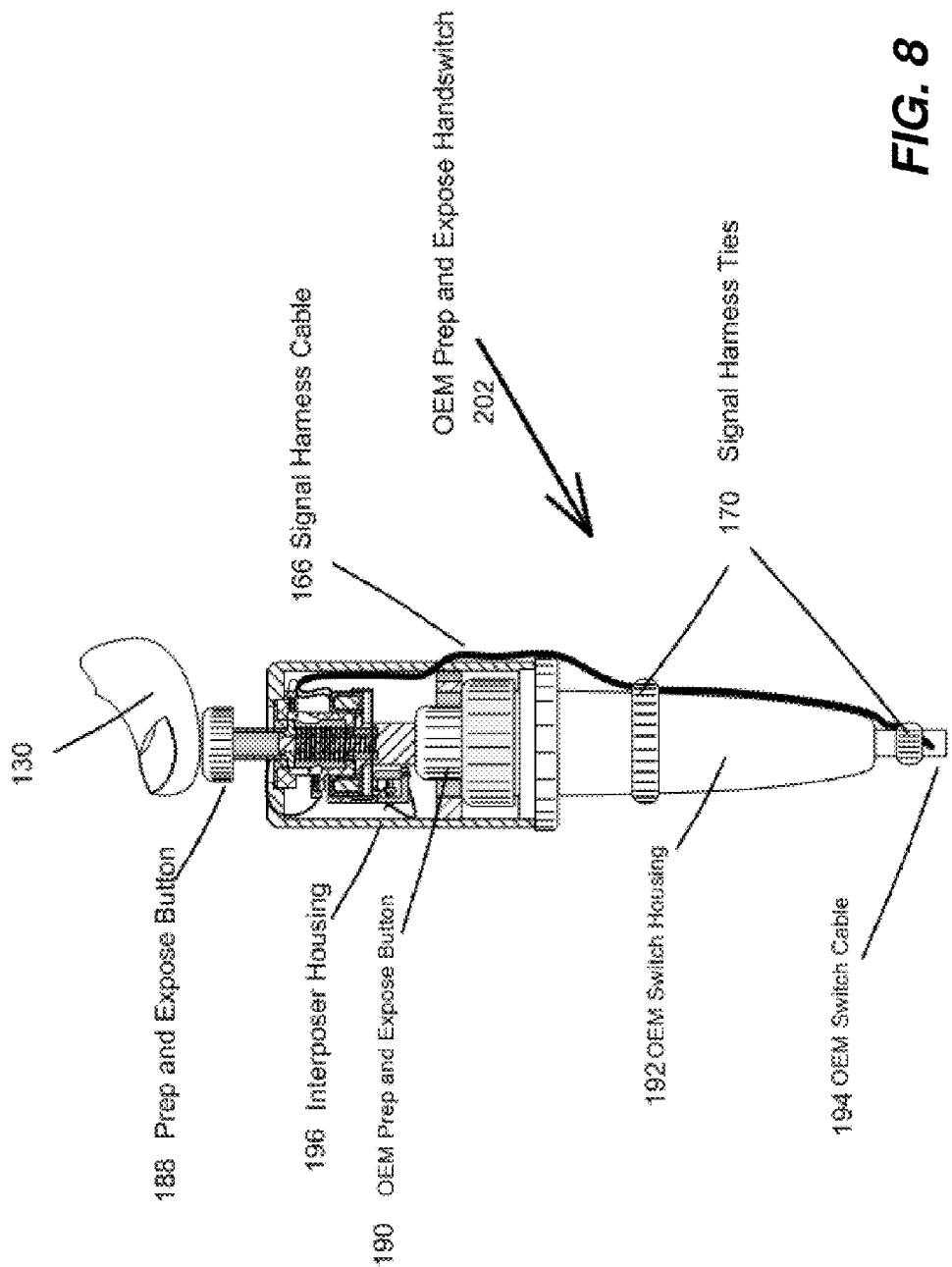
FIG. 8 is a diagram that illustrates exemplary Prep and Expose Switch Interposer mechanism mounted to an OEM single, dual position, Prep and Expose button.

FIG. 8 is a diagram that illustrates an exemplary embodiment of a retrofit mechanism that can serve the purpose of interposing between a DR detector system and a single, dual position, Prep and Expose manual actuator for an analog x-ray imaging system. As shown in FIG. 8, Prep and Expose Switch Interposer mechanism 204 can be coupled to an OEM Prep and Expose Hand switch 202. Prep and Expose Switch Interposer mechanism 204 can be enclosed in Interposer Housing 196 that can fit securely over an existing x-ray system hardware Prep and Expose Hand switch 202. Interposer Housing 196 can be securely attached to OEM Switch Housing 192 by means of screws or glue or any other physical means. Interposer Housing 196 can have a detachable, replaceable or permanent attachment to OEM Switch Housing 192. Signal Harness Cable 166 can contain some or all signal wires and solenoid energization wires and can exit Interposer Housing 196 through an access hole in the housing wall. Signal Harness Cable 166 can then attached to the existing OEM Switch Housing 192 and/or OEM Switch Cable 194 by Signal Harness Ties 170. Signal Harness Cable 166 can connect to the DR detector system electronics such as Interface and Control Circuit 30 shown earlier. In one embodiment, signals from some or all signal wires can be collected and wirelessly transmitted to the DR detector system (e.g., from inside Interposer housing 196 or after exiting Interposer Housing 196).

Pressure applied by Operator finger 130 can exert force onto Prep and Expose Button 188 down through components of Prep and Expose Switch Interposer mechanism 204 to OEM Prep and Expose Button 190.

Figure 9A:
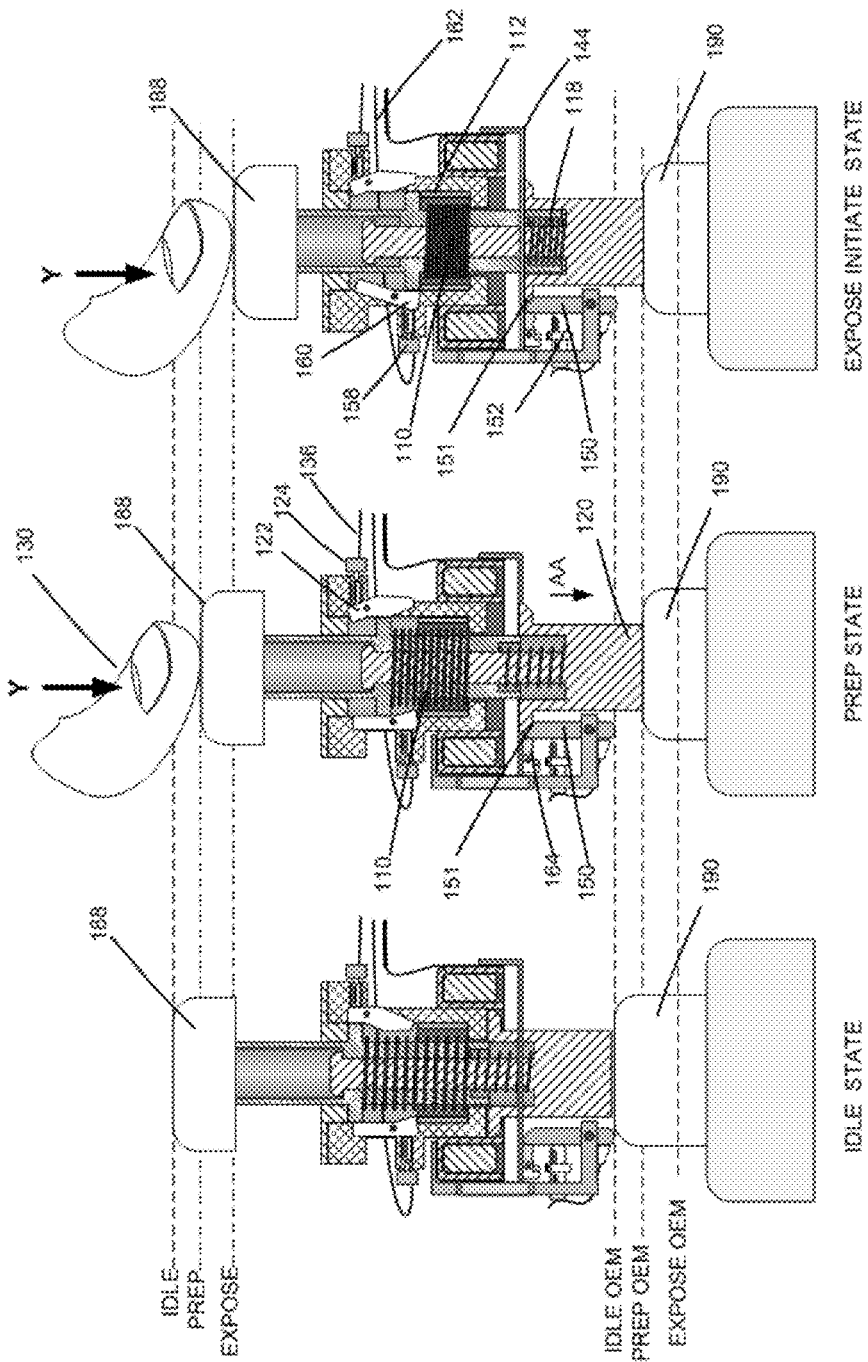
FIG. 9A and FIG. 9B are diagrams that illustrate another exemplary Expose sequence embodiment according to the application.
Figure 9B:
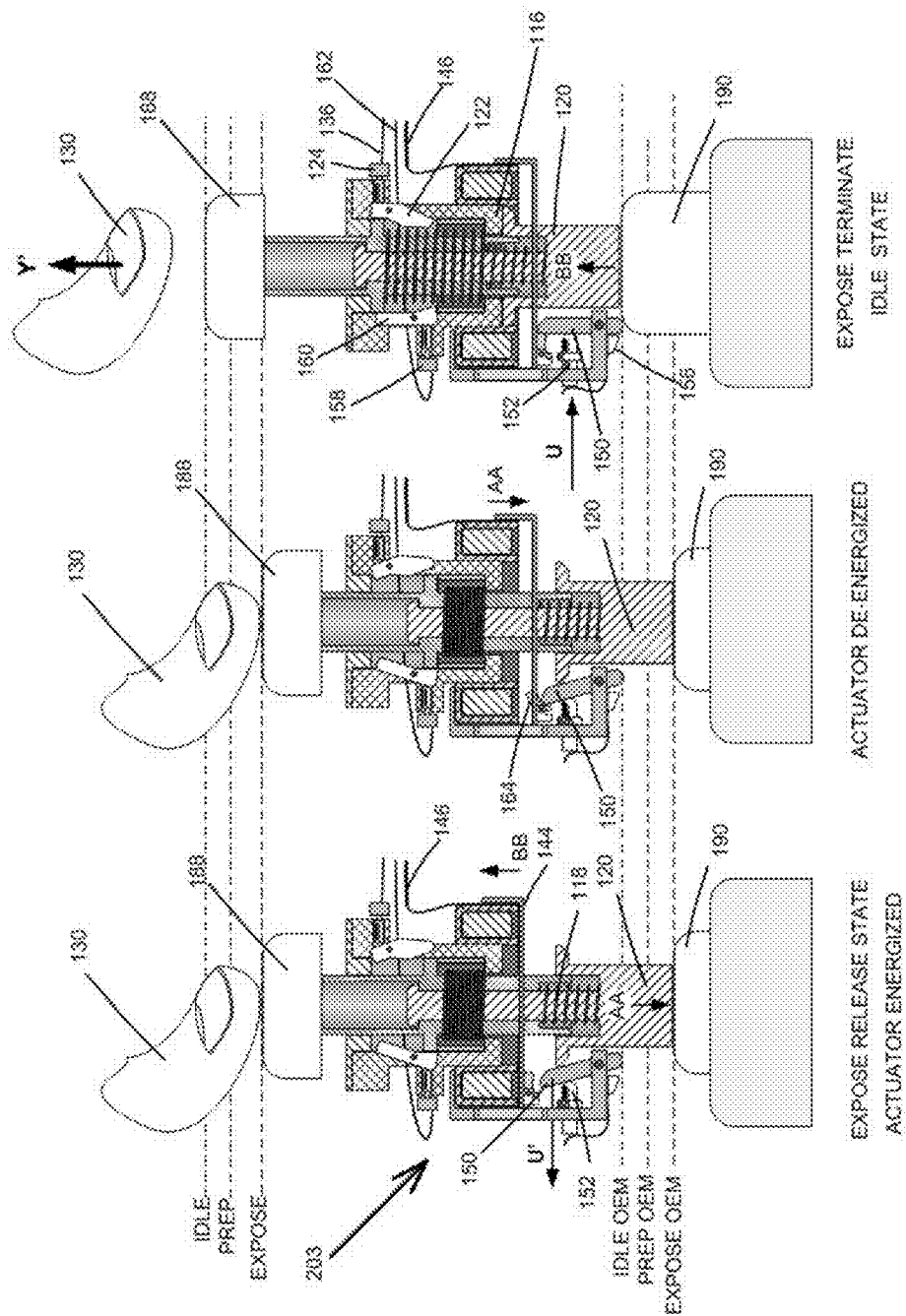

Certain exemplary embodiments for single button interposer mechanisms for DR retrofit to an existing radiographic imaging system can operate similarly to previous embodiments except in this case there can be three positions of OEM Prep and Expose Button 190 for the IDLE, PREP and EXPOSE positions (e.g., illustrated in FIGS. 9A and 9B).

Three mechanism states for Prep and Expose Switch Interposer mechanism 204 can be as follows: the IDLE STATE or not pressed condition, the PREP STATE where the input Prep and Expose Button 188 is partially pressed (e.g., to a portion such as one half of its full travel distance) and the EXPOSE INITIATE STATE where the input Prep and Expose Button 188 can be fully depressed as shown in FIG. 9A. Exemplary physical positions for input Prep and Expose Button 188 and the output OEM Prep and Expose Button 190 are shown respectively by labeled horizontal dashed lines in FIG. 9A.

As shown in FIG. 9A, a default IDLE STATE can have no operator input and Prep and Expose Button 188 can rest at the IDLE position and an output OEM Prep and Expose Button 190 can rest at the IDLE OEM position. The PREP STATE can begin when Operator finger 130 presses in direction Y and moves Prep and Expose Button 188 to the PREP position. Actuator Button Plunger 120 can then force the output OEM Prep and Expose Button 190 to the PREP OEM position. At this point OEM Prep and Expose Hand switch 202 of FIG. 5 can send a Prep signal, through OEM Switch Cable 194 in FIG. 8, to the existing x-ray system hardware to prepare for an x-ray exposure. For example, preparing for an x-ray exposure can include causing the x-ray generator rotor to begin to spin up to speed. In the PREP STATE, Cam Lever 122 can pivot and deactivate Prep Micro Switch 124 to send a Prep state change signal through Prep Micro switch signal wire 136 to the DR detector system controller and software. In one embodiment, the Prep state change signal can be sent through Interface and Control Circuit 30.

For the third EXPOSE INITIATE STATE, Operator finger 130 can press Prep and Expose Button 188 further down in direction Y to the EXPOSE position. However, a corresponding motion of the OEM Prep and Expose Button 190 can not happen at this point because Plunger Stop Lever 150 operates to interfere. Actuator Button Plunger Spring 118 now becomes fully compressed because Actuator Button Plunger 120 can be locked by Plunger Stop Lever 150 at Actuator-Stop Interface 151. Further, Button Stem Spring 110 can also be fully compressed as Button Stem Flange 106 is forced down against Button Travel Limit 112.

At this position, input Prep and Expose Button 188 can cause Cam Lever 160 to rotate and actuate Expose Micro Switch 158 to send a signal through Expose Micro switch signal wire 162 to the DR detector system indicating that the switch mechanism has changed to the EXPOSE INITIATE state. The signal from Expose Micro Switch 158 can initiate operations including a reset operation in the DR detector system. When reset, the DR detector system can send a reset confirmation message to a controller such as Interface and Control Circuit 30, in FIG. 13, to indicate the DR detector system can now receive an x-ray exposure.

Three additional states of Prep and Expose Switch Interposer mechanism 204 are shown in FIG. 9B. These states can be: the EXPOSE RELEASE STATE, the ACTUATOR DE-ENERGIZED STATE and the EXPOSE TERMINATE STATE. The EXPOSE RELEASE state can occur while Operator finger 130 continues to press input Prep and Expose Button 188 and after the DR detector system has sent a reset confirmation message indicating its ready condition to receive an x-ray exposure. Current can now be sent (e.g., by DR detector system) through Coil Wires 146 to energize Solenoid Release Actuator 203, which can cause Armature 144 with Stop Lever Catch 164 to lift up and release Actuator Button Plunger 120 that can travel down in direction AA with force from Actuator Button Plunger Spring 118. This force pushes OEM Prep and Expose Button 190 to the EXPOSE OEM position thereby triggering the x-ray generator to fire.

From this point on the DR detector system can integrate energy from the x-ray beam to form a diagnostic image until the preconfigured DR detector system integration time expires or an integration stop signal is received by the DR detector system.

The current sent through Coil Wires 146 can be of a very brief duration lasting on the order of several tenths of seconds. Immediately after the current pulse is turned off, Armature 144 returns to the un-energized position in the ACTUATOR DE-ENERGIZED state. Stop Lever Catch 164 falls, along with Armature 144, and can strike Plunger Stop Lever 150. Stop Lever Catch 164 can pivot up and away to resist or prevent interference with Plunger Stop Lever 150. During the ACTUATOR DE-ENERGIZED state the output OEM Prep and Expose Button 190 can remain at the EXPOSE OEM position as long as pressure from Operator finger 130 continues. Normally, this will be longer than the time of the x-ray exposure. In one embodiment, the Operator finger pressure can continue until the operator hears the x-ray source exposure begin and/or end.

When Operator finger 130 is pulled up away from the input Prep and Expose Button 188 in direction Y', the input Prep and Expose Button 188 can return to the IDLE position by the stored force from Button Stem Spring 110, which at the same time, can lift Actuator Button Plunger 120 back up against Button Stem Receiver 116.

It can be seen from FIGS. 9A and 9B that OEM Prep and Expose Button 190 can only be depressed to a PREP position by force from Operator finger 130. Likewise, OEM Prep and Expose Button 190 can only be depressed to the EXPOSE position by force from Operator finger 130 and then only when Solenoid Release Actuator 203 has been energized, which can occur only after the DR detector system is ready to receive an x-ray exposure.

Certain exemplary embodiments of a retrofit mechanism that can serve the purpose of interposing between a DR detector system and an existing x-ray system hardware installation can include an alert (e.g., audible, visual, displayed in a viewable display, etc.) to indicate operational status of the expose request or expose button activation by the operator. In one embodiment, an alert can be a visual indicator such as a visible light and/or audible indicator to indicate the expose status to the operator. For example, upon the Expose button (e.g., 188, 104) push by the operator, a visual indicator can be set red to indicate that the conditions for the x-ray radiation by the radiographic imaging system are not yet satisfied (e.g., the DR receiver panel 40 is not reset). In one embodiment, a short beeping sound can occur at this point. Upon indication (e.g., reset ack receipt) of the reset or readiness of the DR detector, the visual indicator can be set to green (e.g., and the actuator 164 in a second non-blocking position), and at this point the expose button (e.g., 138, 190) is operated by the operator for the existing console to sent the expose signal to the x-ray tube (e.g., 24). In one embodiment, a continuous beeping sound (or different sound) can occur at this point, which indicates to the operator that the x-ray tube has initiated x-ray emission so the operator can remove their finger from the expose button (e.g., 188, 104). In existing radiographic imaging systems, the operator can hold the expose button (or prep and expose buttons) until they hear the x-ray tube fire (emit x-ray radiation) because the x-ray tube firing can generate substantial noise. The alert can further change (e.g., another color or turned off), by monitoring conditions such as but not limited to x-ray emission termination and/or an integration period by the DR receiver 14. FIGS. 4A-4B show an optional alert (e.g., LED) 147 that can be connected using wire 147a.

In one embodiment, the exemplary visual/audible indicator can further be used by the retrofit apparatus in coordination with the analog mode. For example, upon actuation of a bypass switch (e.g., Lockout Override Lever 172) by the operator, the visual indicator can be set yellow (e.g., and/or a third different sound) to indicate that the DR receiver panel 40 will not be used and that film or CR operations/timing can be performed by the radiographic imaging system.

In one embodiment, the retrofit apparatus (e.g., 200, 201, 204) can provide a sensory indication to the operator when an exemplary Switch Interposer mechanism (e.g., actuator 164) is moved to a non-blocking position (e.g., by an additional sideways and/or vertical movement of the expose button 188, 104). Thus, the operator can feel movement and/or actuation of the OEM Prep and/or Expose buttons.

Embodiments of methods and/or apparatus according to the application can provide various advantages. For example, retrofit apparatus embodiments and/or retrofit methods can retain the ability to use the imaging system with film or CR receivers as well as allowing the use of DR receivers (e.g., dual mode or mode selection). There would be advantages to retrofit apparatus embodiments and/or retrofit methods that can mount over existing film or CR type radiographic imaging systems/console without modification. Further, there would be advantages to retrofit apparatus embodiments and/or retrofit methods that can not actuate either a Prep radiographic imaging event and/or an Expose radiographic imaging event under any circumstance without operator participation. In addition, certain exemplary embodiments do not produce force to activate or press existing film or CR type radiographic imaging systems/console buttons, and therefore retrofit apparatus can be both compact and/or low power. In at least one exemplary embodiment, an additional component can bypass or override the retrofit apparatus, which can allow an existing film or CR type radiographic imaging systems/console to be operated without removal (e.g., without power to the retrofit apparatus or without an operational retrofit apparatus) of the retrofit apparatus for film or CR mode.

Exemplary embodiments herein can be applied to digital radiographic imaging panels that use an array of pixels comprising an X-ray absorbing photoconductor and a readout circuit (e.g., direct detectors). Since the X-rays are absorbed in the photoconductor, no separate scintillating screen is required.

It should be noted that while the present description and examples are primarily directed to radiographic medical imaging of a human or other subject, embodiments of apparatus and methods of the present application can also be applied to other radiographic imaging applications. This includes applications such as non-destructive testing (NDT), for which radiographic images may be obtained and provided with different processing treatments in order to accentuate different features of the imaged subject.

Embodiments of radiographic imaging systems and/methods described herein contemplate methods and program products on any computer readable media for accomplishing its operations. Certain exemplary embodiments accordingly can be implemented using an existing computer processor, or by a special purpose computer processor incorporated for this or another purpose or by a hardwired system.

Consistent with exemplary embodiments, a computer program with stored instructions that perform on image data accessed from an electronic memory can be used. As can be appreciated by those skilled in the image processing arts, a computer program implementing embodiments herein can be utilized by a suitable, general-purpose computer system, such as a personal computer or workstation. However, many other types of computer systems can be used to execute computer programs implementing embodiments, including networked processors. Computer program for performing method embodiments or apparatus embodiments may be stored in various known computer readable storage medium (e.g., disc, tape, solid state electronic storage devices or any other physical device or medium employed to store a computer program), which can be directly or indirectly connected to the image processor by way of the internet or other communication medium. Those skilled in the art will readily recognize that the equivalent of such a computer program product may also be constructed in hardware. Computer-accessible storage or memory can be volatile, non-volatile, or a hybrid combination of volatile and non-volatile types.

It will be understood that computer program products implementing embodiments of this application may make use of various image manipulation algorithms and processes that are well known. It will be further understood that computer program products implementing embodiments of this application may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with computer program product implementing embodiments of this application, are not specifically shown or described herein and may be selected from such algorithms, systems, hardware, components and elements known in the art.

While the invention has been illustrated with respect to one or more implementations, alterations and/or modifications can be made to the illustrated examples without departing from the spirit and scope of the appended claims. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only. The scope of the invention is indicated by the appended claims, and all changes that come within the meaning and range of equivalents thereof are intended to be embraced therein.

What is claimed is:

1. A method for obtaining an image using a digital radiography receiver in an x-ray imaging system of a type configured for film or computed radiography, where the x-ray imaging system includes a manual operator control for generating and transmitting an expose signal to an x-ray generator of the x-ray imaging system, the method comprising:
   providing a retrofit connection apparatus that adapts the x-ray imaging system for use with the digital radiography (DR) receiver by:
   forming a receiver interface channel for communicating signals to and from the DR receiver;
   providing an operator actuated interposer control switch with a releasable mechanical stop, including the interposer control switch transmitting an initiate signal to the DR receiver when the operator actuates the interposer control switch against the releasable mechanical stop;
   where in response to the operator actuating the interposer control switch the releasable mechanical stop is configured to release upon receiving a reset current activated by the DR receiver when the DR receiver receives the initiate signal and completes a reset procedure; and activating the manual operator control to transmit the expose signal to the x-ray generator responsive to the mechanical stop being released.

2. The method of claim 1, further comprising:

sensing actuation of the interposer control switch; and resetting the DR receiver.

3. The method of claim 2, where the retrofit apparatus comprises an electromechanical actuator to provide the releasable mechanical stop.

4. The method of claim 2, further comprising providing a single button on the interposer control switch to implement reset of the DR receiver and to transmit the expose signal.

5. The method of claim 1, further comprising:

providing a second operator actuated control switch;

sensing actuation of the second operator actuated control switch; and changing a power state of the DR receiver and readiness of the x-ray generator responsive to the actuation of the second operator actuated control switch.

6. The method of claim 1, further comprising resisting the generation of the expose signal until the reset of the DR receiver is acknowledged.

7. The method of claim 6, further comprising acknowledging the reset of the DR receiver by sending a return signal or by an elapsed time interval.

8. The method of claim 1, where providing the retrofit connection apparatus does not modify an exterior or interior of the x-ray imaging system.

9. The method of claim 1, where the retrofit connection apparatus does not apply force in the direction of activation of the manual operator control for generating the exposure signal.

10. The method of claim 1, where the retrofit apparatus comprises a switch controller configured to cover a first switch on a control panel and configured to control the operation of the first switch by an operator according to the operation of a second switch by the operator, where the second switch is mounted on the switch controller mounted to the x-ray imaging system.

11. The method of claim 1, further comprising:

providing the retrofit connection apparatus a first mode for operating the x-ray imaging system with the DR receiver; and providing the retrofit connection apparatus a second mode for operating the x-ray imaging system with an x-ray film cassette or a computed radiography cassette, wherein the x-ray film cassette and the computer radiography cassette are removed from the x-ray imaging system to output an image and the DR receiver is not removed from the x-ray imaging system to output an image.

12. The method of claim 11, where the second mode performs an alternate timing sequence where the expose signal is transmitted directly to the x-ray generator.

13. The method of claim 1, further comprising providing a bypass actuator to allow operation of the x-ray imaging system in a CR or analog mode.

14. The method of claim 1, further comprising providing an alert indicator configured to indicate to the operator two statuses of the manual operator control, where the alert is an audible alert indicator or a visual alert indicator.

15. An apparatus for x-ray imaging configured to use a digital radiography receiver in an x-ray imaging system of a type configured for film or computed radiography, comprising:

a generator interface channel to communicate with the x-ray imaging system;

a manual operator control to generate a preparation signal and an expose signal;

an interposer component installed as a retrofit to the x-ray imaging system, the interposer component comprising:

a plunger;

a mechanical stop to limit movement of the plunger in response to an operator actuation of the interposer component;

a release mechanism to release the mechanical stop in response to a signal indicating that the digital radiography receiver has been reset; and a receiver interface channel to communicate with the digital radiography receiver, where in response to the signal indicating that the digital radiography receiver has been reset, the release mechanism is configured to release the mechanical stop to allow the plunger to activate the manual operator control and generate the expose signal.

16. The apparatus of claim 15, where the retrofit interposer component comprises a mode selector to select a first mode setting for image capture using the digital radiography receiver and a second mode setting for image capture using a removable film or computed radiography cassette, and where the expose signal is transmitted to the x-ray generator over the generator interface channel responsive to the activation of the manual operator control.

17. The method of claim 1, further comprising the reset current generating a magnetic field in the interposer control switch for releasing the mechanical stop.

18. The method of claim 17, further comprising extending a plunger in the interposer control switch using a compressed spring responsive to releasing the mechanical stop.

19. The method of claim 18, wherein the step of activating the manual operator control comprises the plunger contacting the manual operator control.

* * * * *